(12) United States Patent
Allen et al.

(10) Patent No.: US 6,909,031 B2
(45) Date of Patent: Jun. 21, 2005

(54) TRANSGENIC MICE CONTAINING GLUCAGON RECEPTOR GENE DISRUPTIONS

(75) Inventors: Keith D. Allen, Cary, NC (US); Mark Moore, Redwood City, CA (US); William Matthews, Woodside, CA (US)

(73) Assignee: Deltagen, Inc., Redwood City, CA (US)

( * ) Notice: Subject to any disclaimer, the term of this patent is extended or adjusted under 35 U.S.C. 154(b) by 0 days.

(21) Appl. No.: 10/010,065

(22) Filed: Dec. 5, 2001

(65) Prior Publication Data

US 2002/0144300 A1 Oct. 3, 2002

Related U.S. Application Data

(60) Provisional application No. 60/251,804, filed on Dec. 6, 2000, provisional application No. 60/266,044, filed on Feb. 1, 2001, and provisional application No. 60/271,121, filed on Feb. 23, 2001.

(51) Int. Cl.[7] ...................... A01K 67/027; C12N 15/00; C12N 5/00; C12N 5/02; C12N 5/06
(52) U.S. Cl. .............................. 800/18; 800/21; 800/25; 435/325; 435/354
(58) Field of Search ................................ 800/8, 18, 21, 800/14; 435/325

(56) References Cited

PUBLICATIONS

Leonard, 1995, Immunological Reviews, vol. 148, pp. 97–114.*
Griffiths, 1993, Microscopy Research and Technique, vol. 41, pp. 344–358.☐☐☐☐.*
Mullins, 1996, J. Clin. Invest., vol. 98, pp. S37–S40.*
Campbell and Wilmut, 1997, Theirogenology, vol. 47, pp. 63–72.*
McGreath, 2000, Nature, vol. 405, pp. 1066–1069.*
Kent–First, 2000, Natue Biotecnology, vol. 18, pp. 928–929.*
Dinnyes, 2002, Cloning and Stem Cells, vol. 4, pp. 81–90.*
Capecchi, 1994, Scientific American, vol. 270, pp. 34–41.*
Burcelin, 1995, Gene, vol. 164, pp. 305–310.*
A. Saltiel, "New Perspectives into the Molecular Pathogenesis and Treatment of Type 2 Diabetes," Cell, vol. 104, Feb. 23, 2001, pp. 517–529.
R. Unger et al., "The Essential Role of Glucagon in the Pathogenesis of Diabetes Mellitus," The Lancet, Jan. 4, 1975, pp. 14–16.
R. Unger, "Diabetes and the Alpha Cell," Diabetes, vol. 25, Feb. 1976, pp. 136–151.

(Continued)

Primary Examiner—Peter Paras
Assistant Examiner—Valarie Bertoglio
(74) Attorney, Agent, or Firm—John E. Burke

(57) ABSTRACT

The present invention relates to transgenic animals, as well as compositions and methods relating to the characterization of gene function. Specifically, the present invention provides transgenic mice comprising mutations in a glucagon receptor gene. Such transgenic mice are useful as models for disease and for identifying agents that modulate gene expression and gene function, and as potential treatments for various disease states and disease conditions. The present invention also relates to diabetes and diabetic condition, as it demonstrates the role of the glucagon receptor in diabetes and diabetic conditions. The present invention further relates to weight gain and weight related conditions, such as obesity, and demonstrates the role of the glucagon receptor in weight gain and weight related conditions, such as obesity. In accordance with these aspects, the present invention provides methods and compositions useful in identifying, testing, and providing treatments for diabetes and diabetic conditions, weight gain and weight related conditions such as obesity.

7 Claims, 16 Drawing Sheets

```
CAGGGTCTCCCTTGCAACCTGAGGAGAGGTGCACACACTCTGAGGACCTAGGTGTGCAACCTCTGCCAGATGTGGG
GCGTGGCTACCCAGAGGCATGCCCCTCACCCAGCTCCACTGTCCCCACCTGCTGCTGCTGCTGTTGGTGCTGTCAT
GTCTGCCAGAGGCACCCTCTGCCCAGGTAATGGACTTTTTGTTTGAGAAGTGGAAGCTCTATAGTGACCAATGTCA
CCACAACCTAAGCCTGCTGCCCCCACCTACTGAGCTGGTCTGTAACAGAACCTTCGACAACTACTCCTGCTGGCCT
GACACCCCTCCCAACACCACTGCCAACATTTCCTGCCCCTGGTACCTACCTTGGTGCCACAAAGTGCAGCACCGCC
TAGTGTTCAAGAGGTGTGGGCCCGATGGGCAGTGGGTTCGAGGGCCACGGGGGCAGCCGTGGCGCAACGCCTCCCA
ATGTCAGTTGGATGATGAAGAGATCGAGGTCCAGAAGGGGGTGGCCAAGATGTATAGCAGCCAGCAGGTGATGTAC
ACCGTGGGCTACAGTCTGTCCCTGGGGGCCTTGCTCCTTGCGCTGGTCATCCTGCTGGGGCCTCAGGAAGCTGCACT
GCACCCGAAACTACATCCATGGGAACCTGTTTGCGTCCTTTGTGCTCAAGGCTGGCTCTGTGTTGGTCATCGATTG
GCTGCTGAAGACACGGTACAGCCAGAAGATTGGCGATGACCTCAGTGTGAGCGTCTGGCTCAGTGACGGGGCGATG
GCCGGCTGCAGAGTGGCCACAGTGATCATGCAGTACGGCATCATACCCAACTATTGCTGGTTGCTGGTAGAGGGCG
TGTACCTGTACAGCCTGCTGAGCCTTGCCACCTTCTCTGAGAGGAGCTTCTTTTCCCTCTACCTGGGCATTGGCTG
GGGTGCGCCCCTGCTGCTTGTCATCCCCTGGGTGGTGGTCAAGTGTCTGTTTGAGAATGTTCAGTGCTGGACCAGC
AATGACAACATGGGATTCTGGTGGATCCTGCGTATTCCTGTCTTCCTGGCCTTACTGATCAATTTTTCATCTTTG
TCCACATCATTCAACTTCTTGTGGCCAAGCTGCGTGCCCATCAGATGCACTATGCTGATTACAAGTTCCGGCTGGC
CAGGTCCACGCTGACCCTCATCCCTCTGCTGGGGGTCCACGAGGTGGTCTTTGCCTTTGTGACTGACGAGCATGCC
CAAGGCACCCTGCGCTCCACCAAGCTCTTTTTTGACCTGTTCCTCAGCTCCTTCCAGGGTCTGCTGGTGGCTGTTC
TCTACTGTTTCCTCAACAAGGAGGTGCAGGCAGAGCTGATGCGGCGTTGGAGGCAATGGCAAGAAGGCAAAGCTCT
TCAGGAGGAAAGGTTGGCCAGCAGCCATGGCAGCCACATGGCCCCAGCAGGGCCTTGTCATGGTGATCCCTGTGAG
AAACTTCAGCTTATGAGTGCAGGCAGCAGCAGTGGGACTGGCTGTGTGCCCTCTATGGAGACCTCGCTGGCCAGTA
GTCTCCCAAGGTTGGCTGACAGCCCCACCTGAATCTCCACTTGGAGCCTAGGCAGGTTGTGTTCAAGAAAGGGCCT
CAGAGGACAACCCAGAGCCAGATGCCCGGCCAAGGTTGAAGAGCCAAAGCAAGCAAGACAGCAGCTTGTACTGTGCA
CACTCCCCTAACCTGTCCTAGCCTGGCACAGGCCACAGTGACAGAGTAGGGGTTGGATATGATGGAGAAGCCATGT
TATCTATGAACTCTGAGTGTTCCCATGTGTGTTGACATGGTCCCTGTACCCAGATATGTCCTTCAGTAAAAAGCTC
GAGTGGAGCTGCTGCACAGCTCGTGGACAGCAGGCTTGAAGCCCCCAGGGACGGGGTTTGGGAGGCCGGGGATGAG
CAGCACACTCAGCAGGTGGAGCGCTAGTGCAACCCAGGAAAGAA (SEQ ID NO:1)
```

OTHER PUBLICATIONS

R. Burcelin et al., "Cloning and Sequence Analysis of the Murine Glucagon Receptor–Encoding Gene," Gene, vol. 164, May 1995, pp. 305–310.

C. Unson et al., "Biological Activities of des–His 1 [Glu9] Glucagon Amide, A Glucagon Antagonisti," Peptides, vol. 10, May 1989, pp. 1171–1177.

M. Wakelam et al., "Activation of Two Signal–Transdcuction Systems in Hepatocytes by Glucagon," Nature, vol. 323, Sep. 4, 1986, pp. 68–71.

R. Pittner et al., "Acitvation of Membrane Protein Kinase C By Glucagon and Ca2+–Mobilizing Hormones in Cultured Rat Hepatocytes," Biochem. J., vol. 277, Mar. 1991, pp. 371–378.

S Chambers et al., "Glucagon Receptor Gene Mutation in Essential Hypertension" Nature Genetics, vol. 12, Feb. 1996, pp. 122.

J. Hager et al., "A Missense Mutation in the Glucagon Receptor Gene is Associated with Non–Insulin–Dependent Diabetes Mellitus," Nature Genetics, vol. 9, Mar. 1995, pp. 299–304.

S. Lok et al., "The Human Glucagon Receptor Encoding Gene: Structure, CDNA Sequence and Chromosomal Localization" Gene, vol. 140, 1994, pp. 203–209.

S. Menzel et al., "Localization of the Glucagon Receptor Gene to Human Chromosome Band 17q25" Genomics, vol. 20, 1994, pp. 327–328.

* cited by examiner

```
CAGGGTCTCCCTTGCAACCTGAGGAGAGGTGCACACACTCTGAGGACCTAGGTGTGCAACCTCTGCCAGATGTGGG
GCGTGGCTACCCAGAGGCATGCCCCTCACCCAGCTCCACTGTCCCCACCTGCTGCTGCTGCTGTTGGTGCTGTCAT
GTCTGCCAGAGGCACCCTCTGCCCAGGTAATGGACTTTTTGTTTGAGAAGTGGAAGCTCTATAGTGACCAATGTCA
CCACAACCTAAGCCTGCTGCCCCCACCTACTGAGCTGGTCTGTAACAGAACCTTCGACAACTACTCCTGCTGGCCT
GACACCCCTCCCAACACCACTGCCAACATTTCCTGCCCCTGGTACCTACCTTGGTGCCACAAAGTGCAGCACCGCC
TAGTGTTCAAGAGGTGTGGGCCCGATGGGCAGTGGGTTCGAGGGCCACGGGGGCAGCCGTGGCGCAACGCCTCCCA
ATGTCAGTTGGATGATGAAGAGATCGAGGTCCAGAAGGGGGTGGCCAAGATGTATAGCAGCCAGCAGGTGATGTAC
ACCGTGGGCTACAGTCTGTCCCTGGGGGCCTTGCTCCTTGCGCTGGTCATCCTGCTGGGCCTCAGGAAGCTGCACT
GCACCCGAAACTACATCCATGGGAACCTGTTTGCGTCCTTTGTGCTCAAGGCTGGCTCTGTGTTGGTCATCGATTG
GCTGCTGAAGACACGGTACAGCCAGAAGATTGGCGATGACCTCAGTGTGAGCGTCTGGCTCAGTGACGGGGCGATG
GCCGGCTGCAGAGTGGCCACAGTGATCATGCAGTACGGCATCATACCCAACTATTGCTGGTTGCTGGTAGAGGGCG
TGTACCTGTACAGCCTGCTGAGCCTTGCCACCTTCTCTGAGAGGAGCTTCTTTTCCCTCTACCTGGGCATTGGCTG
GGGTGCGCCCCTGCTGTTTGTCATCCCCTGGGTGGTGGTCAAGTGTCTGTTTGAGAATGTTCAGTGCTGGACCAGC
AATGACAACATGGGATTCTGGTGGATCCTGCGTATTCCTGTCTTCCTGGCCTTACTGATCAATTTTTTCATCTTTG
TCCACATCATTCAACTTCTTGTGGCCAAGCTGCGTGCCCATCAGATGCACTATGCTGATTACAAGTTCCGGCTGGC
CAGGTCCACGCTGACCCTCATCCCTCTGCTGGGGGTCCACGAGGTGGTCTTTGCCTTTGTGACTGACGAGCATGCC
CAAGGCACCCTGCGCTCCACCAAGCTCTTTTTTGACCTGTTCCTCAGCTCCTTCCAGGGTCTGCTGGTGGCTGTTC
TCTACTGTTTCCTCAACAAGGAGGTGCAGGCAGAGCTGATGCGGCGTTGGAGGCAATGGCAAGAAGGCAAAGCTCT
TCAGGAGGAAAGGTTGGCCAGCAGCCATGGCAGCCACATGGCCCCAGCAGGGCCTTGTCATGGTGATCCCTGTGAG
AAACTTCAGCTTATGAGTGCAGGCAGCAGCAGTGGGACTGGCTGTGTGCCCTCTATGGAGACCTCGCTGGCCAGTA
GTCTCCCAAGGTTGGCTGACAGCCCCACCTGAATCTCCACTTGGAGCCTAGGCAGGTTGTGTTCAAGAAAGGGCCT
CAGAGGACAACCCAGAGCCAGATGCCCGGCCAAGGTTGAAGAGCCAAAGCAGCAAGACAGCAGCTTGTACTGTGCA
CACTCCCCTAACCTGTCCTAGCCTGGCACAGGCCACAGTGACAGAGTAGGGGTTGGATATGATGGAGAAGCCATGT
TATCTATGAACTCTGAGTGTTCCCATGTGTGTTGACATGGTCCCTGTACCCAGATATGTCCTTCAGTAAAAAGCTC
GAGTGGAGCTGCTGCACAGCTCGTGGACAGCAGGCTTGAAGCCCCCAGGGACGGGGTTTGGGAGGCCGGGGATGAG
CAGCACACTCAGCAGGTGGAGCGCTAGTGCAACCCAGGAAAGAA  (SEQ ID NO:1)
```

FIGURE 1A

MPLTQLHCPHLLLLLLVLSCLPEAPSAQVMDFLFEKWKLYSDQCHHNLSLLPPPTELVCNRTFDNYSCWPDTPPNT
TANISCPWYLPWCHKVQHRLVFKRCGPDGQWVRGPRGQPWRNASQCQLDDEEIEVQKGVAKMYSSQQVMYTVGYSL
SLGALLLALVILLGLRKLHCTRNYIHGNLFASFVLKAGSVLVIDWLLKTRYSQKIGDDLSVSVWLSDGAMAGCRVA
TVIMQYGIIPNYCWLLVEGVYLYSLLSLATFSERSFFSLYLGIGWGAPLLFVIPWVVVKCLFENVQCWTSNDNMGF
WWILRIPVFLALLINFFIFVHIIQLLVAKLRAHQMHYADYKFRLARSTLTLIPLLGVHEVVFAFVTDEHAQGTLRS
TKLFFDLFLSSFQGLLVAVLYCFLNKEVQAELMRRWRQWQEGKALQEERLASSHGSHMAPAGPCHGDPCEKLQLMS
AGSSSGTGCVPSMETSLASSLPRLADSPT (SEQ ID NO:2)

FIGURE 1B underlined = deleted in targeting construct bold = sequence flanking Neo insert in targeting construct

```
CAGGGTCTCCCTTGCAACCTGAGGAGAGGTGCACACACTCTGAGGACCTAGGTGTGCAAC
CTCTGCCAGATGTGGGGCGTGGCTACCCAGAGGCATGCCCCTCACCCAGCTCCACTGTCC
CCACCTGCTGCTGCTGCTGTTGGTGCTGTCATGTCTGCCAGAGGCACCCTCTGCCCAGGT
AATGGACTTTTTGTTTGAGAAGTGGAAGCTCTATAGTGACCAATGTCACCACAACCTAAG
CCTGCTGCCCCCACCTACTGAGCTGGTCTGTAACAGAACCTTCGACAACTACTCCTGCTG
GCCTGACACCCCTCCCAACACCACTGCCAACATTTCCTGCCCCTGGTACCTACCTTGGTG
CCACAAAGTGCAGCACCGCCTAGTGTTCAAGAGGTGTGGGCCCGATGGGCAGTGGGTTCG
AGGGCCACGGGGGCAGCCGTGGCGCAACGCCTCCCAATGTCAGTTGGATGATGAAGAGAT
CGAGGTCCAGAAGGGGGTGGCCAAGATGTATAGCAGCCAGCAGGTGATGTACACCGTGGG
CTACAGTCTGTCCCTGGGGGCCTTGCTCCTTGCGCTGGTCATCCTGCTGGGCCTCAGGAA
GCTGCACTGCACCCGAAACTACATCCATGGGAACCTGTTTGCGTCCTTTGTGCTCAAGGC
TGGCTCTGTGTTGGTCATCGATTGGCTGCTGAAGACACGGTACAGCCAGAAGATTGGCGA
TGACCTCAGTGTGAGCGTCTGGCTCAGTGACGGGGCGATGGCCGGCTGCAGAGTGGCCAC
AGTGATCATGCAGTACGGCATCATACCCAACTATTGCTGGTTGCTGGTAGAGGGCGTGTA
CCTGTACAGCCTGCTGAGCCTTGCCACCTTCTCTGAGAGGAGCTTCTTTTCCCTCTACCT
GGGCATTGGCTGGGGTGCGCCCCTGCTGTTTGTCATCCCCTGGGTGGTGGTCAAGTGTCT
GTTTGAGAATGTTCAGTGCTGGACCAGCAATGACAACATGGGATTCTGGTGGATCCTGCG
TATTCCTGTCTTCCTGGCCTTACTGATCAATTTTTTCATCTTTGTCCACATCATTCAACT
TCTTGTGGCCAAGCTGCGTGCCCATCAGATGCACTATGCTGATTACAAGTTCCGGCTGGC
CAGGTCCACGCTGACCCTCATCCCTCTGCTGGGGGTCCAC**GAGGTGGTCTTTGCCTTTGT
GACTGACGAGCATGCCCAAGGCACCCTGCGCTCCACCAAGCTCTTTTTTGACCTGTTCCT
CAGCTCCTTCCAGGG**TCTGCTGGTGGCTGTTCTCTACTGTTTCCTCAACAAGGAGGTGCA
GGCAGAGCTGATGCGGCGTTGGAGGCAATGGCAAGAAGGCAAAGCTCTTCAGGAGGAAAG
GTTGGCCAGCAGCCATGGCAGCCACATGGCCCCAGCAGGGCCTTGTCATGGTGATCCCTG
TGAGAAACTTCAGCTTATGAGTGCAGGCAGCAGCAGTGGGACTGGCTGTGTGCCCTCTAT
GGAGACCTCGCTGGCCAGTAGTCTCCCAAGGTTGGCTGACAGCCCCACCTGAATCTCCAC
TTGGAGCCTAGGCAGGTTGTGTTCAAGAAAGGGCCTCAGAGGACAACCCAGAGCCAGATG
CCCGGCCAAGGTTGAAGAGCCAAAGCAGCAAGACAGCAGCTTGTACTGTGCACACTCCCC
TAACCTGTCCTAGCCTGGCACAGGCCACAGTGACAGAGTAGGGGTTGGATATGATGGAGA
AGCCATGTTATCTATGAACTCTGAGTGTTCCCATGTGTGTTGACATGGTCCCTGTACCCA
GATATGTCCTTCAGTAAAAAGCTCGAGTGGAGCTGCTGCACAGCTCGTGGACAGCAGGCT
TGAAGCCCCCAGGGACGGGGTTTGGGAGGCCGGGGATGAGCAGCACACTCAGCAGGTGGA
GCGCTAGTGCAACCCAGGAAAGAA (SEQ ID NO:1)
```

FIGURE 2A

```
GGATCTGGCAGCGCCGCGAAGACGAGCGGTCACCGGCGCCCGACCCGAGCGCGCCCAGAGGACGGCGGGGAGCCAA
GCCGACCCCGAGCAGCGCCGCGCGGGCCCTGAGGCTCAAAGGGGCAGCTTCAGGGGAGGACACCCCACTGGCCAG
GACGCCCCAGGCTCTGCTGCTCTGCCACTCAGCTGCCCTCGGAGGAGCGTACACACACCAGGACTGCATTGCCC
CAGTGTGCAGCCCCTGCCAGATGTGGGAGGCAGCTAGCTGCCCAGAGGCATGCCCCCCTGCCAGCCACAGCGACCC
CTGCTGCTGTTGCTGCTGCTGCTGGCCTGCCAGCCACAGGTCCCCTCCGCTCAGGTGATGGACTTCCTGTTTGAGA
AGTGGAAGCTCTACGGTGACCAGTGTCACCACAACCTGAGCCTGCTGCCCCCTCCCACGGAGCTGGTGTGCAACAG
AACCTTCGACAAGTATTCCTGCTGGCCGGACACCCCCGCCAATACCACGGCCAACATCTCCTGCCCCTGGTACCTG
CCTTGGCACCACAAAGTGCAACACCGCTTCGTGTTCAAGAGATGCGGGCCCGACGGTCAGTGGGTGCGTGGACCCC
GGGGGCAGCCTTGGCGTGATGCCTCCCAGTGCCAGATGGATGGCGAGGAGATTGAGGTCCAGAAGGAGGTGGCCAA
GATGTACAGCAGCTTCCAGGTGATGTACACAGTGGGCTACAGCCTGTCCCTGGGGGCCCTGCTCCTCGCCTTGGCC
ATCCTGGGGGGCCTCAGCAAGCTGCACTGCACCCGCAATGCCATCCACGCGAATCTGTTTGCGTCCTTCGTGCTGA
AAGCCAGCTCCGTGCTGGTCATTGATGGGCTGCTCAGGACCCGCTACAGCCAGAAAATTGGCGACGACCTCAGTGT
CAGCACCTGGCTCAGTGATGGAGCGGTGGCTGGCTGCCGTGTGGCCGCGGTGTTCATGCAATATGGCATCGTGGCC
AACTACTGCTGGCTGCTGGTGGAGGGCCTGTACCTGCACAACCTGCTGGGCCTGGCCACCCTCCCCGAGAGGAGCT
TCTTCAGCCTCTACCTGGGCATCGGCTGGGGTGCCCCCATGCTGTTCGTCGTCCCCTGGGCAGTGGTCAAGTGTCT
GTTCGAGAACGTCCAGTGCTGGACCAGCAATGACAACATGGGCTTCTGGTGGATCCTGCGGTTCCCCGTCTTCCTG
GCCATCCTGATCAACTTCTTCATCTTCGTCCGCATCGTTCAGCTGCTCGTGGCCAAGCTGCGGGCACGGCAGATGC
ACCACACAGACTACAAGTTCCGGCTGGCCAAGTCCACGCTGACCCTCATCCCTCTGCTGGGCGTCCACGAAGTGGT
CTTTGCCTTCGTGACGGACGAGCACGCCCAGGGCACCCTGCGCTCCGCCAAGCTCTTCTTCGACCTCTTCCTCAGC
TCCTTCCAGGGCCTGCTGGTGGCTGTCCTCTACTGCTTCCTCAACAAGGAGGTGCAGTCGGAGCTGCGGCGGCGTT
GGCACCGCTGGCGCCTGGGCAAAGTGCTATGGGAGGAGCGGAACACCAGCAACCACAGGGCCTCATCTTCGCCCGG
CCACGGCCCTCCCAGCAAGGAGCTGCAGTTTGGGAGGGGTGGTGGCAGCCAGGATTCATCTGCGGAGACCCCCTTG
GCTGGTGGCCTCCCTAGATTGGCTGAGAGCCCCTTCTGAACCCTGCTGGGACCCCAGCTAGGGCTGGACTCTGGCA
CCCAGAGGCGTCGCTGGACAACCCAGAACTGGACGCCCAGCTGAGGCTGGGGGCGGGGGAGCCAACAGCAGCCCCC
ACCTACCCCCCACCCCCAGTGTGGCTGTCTGCGAGATTGGGCCTCCTCTCCCTGCACCTGCCTTGTCCCTGGTGCA
GAGGTGAGCAGAGGAGTCCAGGGCGGGAGTGGGGGCTGTGCCGTGAACTGCGTGCCAGTGTCCCCACGTATGTCGG
CACGTCCCATGTGCATGGAAATGTCCTCCAACAATAAAGAGCTCAAGTGGTCACCGTG (SEQ ID NO:5)
```

FIGURE 3A

```
MPPCQPQRPLLLLLLLLACQPQVPSAQVMDFLFEKWKLYGDQCHHNLSLLPPPTELVCNRTFDKYSCWPDTPANTT
ANISCPWYLPWHHKVQHRFVFKRCGPDGQWVRGPRGQPWRDASQCQMDGEEIEVQKEVAKMYSSFQVMYTVGYSLS
LGALLLALAILGGLSKLHCTRNAIHANLFASFVLKASSVLVIDGLLRTRYSQKIGDDLSVSTWLSDGAVAGCRVAA
VFMQYGIVANYCWLLVEGLYLHNLLGLATLPERSFFSLYLGIGWGAPMLFVVPWAVVKCLFENVQCWTSNDNMGFW
WILRFPVFLAILINFFIFVRIVQLLVAKLRARQMHHTDYKFRLAKSTLTLIPLLGVHEVVFAFVTDEHAQGTLRSA
KLFFDLFLSSFQGLLVAVLYCFLNKEVQSELRRRWHRWRLGKVLWEERNTSNHRASSSPGHGPPSKELQFGRGGGS
QDSSAETPLAGGLPRLAESPF (SEQ ID NO:6)
```

FIGURE 3B

Relationship of Blood Glucose Levels to Severity of Pancreatic Lesions

Serum Insulin Level Results

Relationship of Serum Insulin Levels to Pancreatic Lesion Severity

Serum Glucagon Results

TRANSGENIC MICE CONTAINING GLUCAGON RECEPTOR GENE DISRUPTIONS

RELATED APPLICATIONS

This application claims priority to U.S. Provisional Application No. 60/251,804, filed Dec. 6, 2000; U.S. Provisional Application No. 60/266,044, filed Feb. 1, 2001 and U.S. Provisional Application No. 60/271,121 filed Feb. 23, 2001, the entire contents of each are incorporated herein by reference.

FIELD OF THE INVENTION

The present invention relates to transgenic animals, compositions and methods relating to the characterization of gene function.

BACKGROUND OF THE INVENTION

Diabetes is defined as a state in which carbohydrate and lipid metabolism are improperly regulated by the hormone insulin (For review, see, e.g., Saltiel, Cell 104:517–529 (2000)). Two major forms of diabetes have been identified, type I and II. Type I diabetes represents the minor form of the disease, affecting 5–10% of diabetic patients. It is thought to result from the autoimmune destruction of the insulin-producing beta cells of the pancreatic Islet of Langerhans. Exogenous administration of insulin typically alleviates the pathophysiology. Type II diabetes is the most common form of the disease and is possibly caused by a combination of defects in the mechanisms of insulin secretion and action. Both forms, type I and type II, have similar complications, but distinct pathophysiology.

Glucose is necessary to ensure proper function and survival of all organs. While hypoglycemia produces cell death, chronic hyperglycemia can also result in organ damage. Following a meal, the level of glucose in the blood is elevated. The balance between the utilization and production of glucose is maintained at equilibrium by two opposing hormones, insulin and glucagon. In response to elevated plasma levels of glucose, pancreatic beta cells secrete insulin. Insulin, in turn, acts on muscle, liver and adipose tissues to stimulate glucose uptake into those cells. When plasma levels of glucose decrease, the pancreatic alpha cells secrete glucagon, which in turn stimulates glycolysis in the liver and release of glucose into the bloodstream.

The first stage of type II diabetes is characterized by the failure of muscle and/or other organs to respond to normal circulating concentrations of insulin. This is commonly associated with obesity, a sedentary lifestyle, as well as a genetic predisposition. This is followed by an increase in insulin secretion from the pancreatic beta cells, a condition called hyperinsulinemia. Ultimately, the beta cells can no longer compensate, leading to impaired glucose tolerance, chronic hyperglycemia, and tissue damage.

The action of glucagon on glycolysis in the liver is mediated by the glucagon receptor. It has been reported that the hyperglycemic state of diabetes mellitus is not only due to glucose under-utilization as a result of decreased insulin, but also to the overproduction of glucose due to elevated concentrations of glucagon (See, e.g., Unger, Diabetes 25:136–151 (1976); Unger and Orci, Lancet 1:14–16 (1975)). The murine glucagon receptor cDNA, gene and promoter region was cloned, sequenced, and its tissue distribution studied (See, e.g., Burcelin et al., Gene 164(2):305 (1995)). The 1944 base pair MRNA cds has been deposited in GenBank (Accession No.: L38613; GI No.: 603463). The murine glucagon receptor was found to contain 13 exons located in a region of 4.0 kb. Moreover, this gene encodes a 485-amino-acid protein consisting of seven putative transmembrane domains. The murine glucagon receptor was found to be expressed predominantly in the liver, kidney, adrenal gland, lung and stomach. Lower levels of expression are detected in brown and white adipose tissue, cerebellum, duodenum and heart. A 1000-bp region of the glucagon receptor promoter has been sequenced. This region contains consensus sequences for putative DNA-binding proteins involved in tissue specificity (c/EBP; HNFI) or hormonal regulation (steroid receptor). Other consensus sequences are those known to function in controlling basal promoter activity, such as AP1 and AP2.

Upon the binding of the glucagon receptor with glucagon, a signal to the cell is transduced, thereby triggering glycogen hydrolysis and glucose synthesis. It has been reported that cyclic adenosine monophosphate (cAMP) mediates the effects of glucagon. The binding of glucagon to its cellular receptor activates adenylate cyclase to produce cAMP, raising the levels of intracellular cAMP. Elevation of intracellular levels of cAMP is believed to result in glycogenolysis and gluconeogenesis, with the resultant rise in glucose production by the liver (See, e.g., Unson et al., Peptides 10:1171–1177 (1989)). Other cellular pathways have also been suggested for the stimulation of glycogenolysis and gluconeogenesis. It has also been reported that glucagon binds to receptors in the hepatocyte membrane that are coupled via a G-protein to phospholipase C. This protein causes the breakdown of phosphatidylinositol 4,5 biphosphate to produce the second messengers inositol triphospate and 1,2 diacylglycerol upon the interaction of glucagon and its receptor (See, e.g., Wakelam et al., Nature 323:68–71 (1986); Unson et al., Peptides 10:1171–1177 (1989); Pittner and Fain, Biochem. J. 277:371–378 (1991)).

Obesity is a disease that affects at least 39 million Americans: more than one-quarter of all adults and about one in five children. Each year, obesity causes at least 300,000 excess deaths in the U.S. and costs the country more than $100 billion. Over the last 10 years, the proportion of the U.S. population that is obese has increased from 25 percent to 32 percent. Obesity is measured by Body Mass Index, or BMI, which is a mathematical calculation used to determine if a person is obese or overweight. BMI is calculated by dividing a person's body weight in kilograms by their height in meters squared. A BMI of 30 or greater is considered obese, while a BMI of 25–29.9 is considered overweight. However, the criteria for diagnosis can be misleading for people with more muscle mass and less body fat than normal, such as athletes. Over 70 million Americans are considered overweight. Health problems, including but not limited to cardiovascular disease, blood pressure, Type II diabetes, high cholesterol, gout, certain types of cancer, and osteoarthritis, are associated with overweight conditions and obesity.

Diabetes and diabetic conditions, as well as weight related conditions, such as obesity, are clearly associated with health problems, and the increase in prevalence of these conditions is a cause for concern. A clear need exists for further analysis and, in particular, in vivo characterization of genes, such as the glucagon receptor, to determine their role in dysfunctions and diseases, such as diabetes or obesity, which may play a role in preventing, ameliorating, or correcting dysfunctions or diseases.

SUMMARY OF THE INVENTION

The present invention generally relates to transgenic animals, as well as to compositions and methods relating to the characterization of gene function. In particular, the present invention relates to a gene encoding the glucagon receptor and its role and function in various biological processes and conditions, including diabetes and obesity.

The present invention provides transgenic cells comprising a disruption in a glucagon receptor gene. The transgenic cells of the present invention are comprised of any cells capable of undergoing homologous recombination. Preferably, the cells of the present invention are stem cells and more preferably, embryonic stem (ES) cells, and most preferably, murine ES cells. According to one embodiment, the transgenic cells are produced by introducing a targeting construct into a stem cell to produce a homologous recombinant, resulting in a mutation of the glucagon receptor gene. In another embodiment, the transgenic cells are derived from the transgenic animals described below. The cells derived from the transgenic animals includes cells that are isolated or present in a tissue or organ, and any cell lines or any progeny thereof.

The present invention also provides a targeting construct and methods of producing the targeting construct that when introduced into stem cells produces a homologous recombinant. In one embodiment, the targeting construct of the present invention comprises first and second polynucleotide sequences that are homologous to the glucagon receptor gene. The targeting construct may also comprise a polynucleotide sequence that encodes a selectable marker that is preferably positioned between the two different homologous polynucleotide sequences in the construct. The targeting construct may also comprise other regulatory elements that can enhance homologous recombination.

The present invention further provides non-human transgenic animals and methods of producing such non-human transgenic animals comprising a disruption in a glucagon receptor gene. The transgenic animals of the present invention include transgenic animals that are heterozygous and homozygous for a null mutation in the glucagon receptor gene. In one aspect, the transgenic animals of the present invention are defective in the function of the glucagon receptor gene. In another aspect, the transgenic animals of the present invention comprise a phenotype associated with having a mutation in a glucagon receptor gene.

In one aspect, the transgenic animals of the present invention exhibit abnormalities of the pancreas, in particular, abnormalities of the pancreatic islet cells. In a preferred aspect, the pancreas exhibits at least one of the following characteristics: hyperplasia, hypertrophy, increased cytoplasmic vacuolization, adenomas, and granularity of the pancreatic islet cells. In a most preferred aspect, the adenomas are exhibited in aged animals, and the increased cytoplasmic vacuolization and granularity of the pancreatic cells are exhibited in the adult animals and the aged animals.

In another aspect, the transgenic animals of the present invention exhibit anti-obesity characteristics. In one embodiment of this aspect, the anti-obesity characteristics include one or more of the following: reduced body weight, reduced organ weight, reduced fat as a percentage of body soft tissue, or reduced body weight gain. In a preferred embodiment of this aspect, the reduced body weight gain is seen when the transgenic animals are exposed to a high-fat diet.

In yet another aspect, the transgenic animals exhibit abnormal body shape. In a preferred embodiment, the transgenic animals exhibit dwarfism.

In yet another aspect, the transgenic animals exhibit infertility. In a preferred aspect, infertility is exhibited in female transgenic animals.

In yet another aspect, the transgenic animals of the present invention exhibit anti-diabetes-like characteristics. In one embodiment of this aspect, the anti-diabetes-like characteristics include one or more of the following: decreased serum glucose levels, increased tolerance to a glucose challenge, decreased serum insulin levels, reduced body weight gain, or a decrease in fat as a percentage of body soft tissue. Preferably, the increased tolerance to a glucose challenge is observed before or after exposure to a high-fat diet. In accordance with this aspect, the present invention provides transgenic animals and methods useful for identifying agents that ameliorate symptoms and characteristics of diabetes or similar diseases. In a preferred embodiment, the agent antagonizes or inhibits the activity or function of the glucagon receptor.

The present invention also provides methods of identifying agents capable of affecting a phenotype of a transgenic animal. For example, a putative agent is administered to the transgenic animal and a response of the transgenic animal to the putative agent is measured and compared to the response of a "normal" or wild-type mouse or, alternatively, compared to a transgenic animal control (without agent administration). The invention further provides agents identified according to such methods. The present invention also provides methods of identifying agents useful as therapeutic agents for treating conditions associated with a disruption or other mutation (including naturally occurring mutations) of the glucagon receptor gene.

The present invention further provides a method of identifying agents having an effect on glucagon receptor expression or function. The method includes administering an effective amount of the agent to a transgenic animal, preferably a mouse. The method includes measuring a response of the transgenic animal, for example, to the agent, and comparing the response of the transgenic animal to a control animal, which may be, for example, a wild-type animal or, alternatively, a transgenic animal control. Compounds that may have an effect on glucagon receptor expression or function may also be screened against cells in cell-based assays, for example, to identify such compounds.

The invention also provides cell lines comprising nucleic acid sequences of a glucagon receptor gene. Such cell lines may be capable of expressing such sequences by virtue of operable linkage to a promoter functional in the cell line. Preferably, expression of the glucagon receptor gene sequence is under the control of an inducible promoter. Also provided are methods of identifying agents that interact with the glucagon receptor gene, comprising the steps of contacting the glucagon receptor gene with an agent and detecting an agent/glucagon receptor gene complex. Such complexes can be detected by, for example, measuring expression of an operably linked detectable marker.

The invention further provides methods of treating diseases or conditions associated with a disruption in a glucagon receptor gene, and more particularly, to a disruption in the expression or function of the glucagon receptor gene. In a preferred embodiment, methods of the present invention involve treating diseases or conditions associated with a disruption in the glucagon receptor gene's expression or function, including administering to a subject in need, a therapeutic agent that affects glucagon receptor expression or function. In accordance with this embodiment, the method comprises administration of a therapeutically effective amount of a natural, synthetic, semi-synthetic, or recombinant glucagon receptor gene, glucagon receptor gene products or fragments thereof as well as natural, synthetic, semi-synthetic or recombinant analogs.

The present invention also provides compositions comprising or derived from ligands or other molecules or compounds that bind to or interact with a glucagon receptor, including agonists or antagonists of a glucagon receptor. Such agonists or antagonists of a glucagon receptor include antibodies and antibody mimetics, as well as other molecules that can readily be identified by routine assays and experiments well known in the art.

The present invention further provides methods of treating diseases or conditions associated with disrupted targeted gene expression or function, wherein the methods comprise detecting and replacing through gene therapy mutated or otherwise defective or abnormal glucagon receptor genes.

The present invention demonstrates the role and function of the glucagon receptor in diabetes and diabetic conditions. The present invention also demonstrates the role of the glucagon receptor in weight gain and weight related conditions, such as obesity. In accordance with these aspects, the present invention provides methods and compositions useful in identifying, testing, and providing treatments for diabetes and diabetic conditions, weight gain and weight related conditions such as obesity. Such methods and compositions include the human glucagon receptor gene as shown in SEQ ID NO:5 (also shown and identified in GenBank GI number: 4503946; Accession number: NM_000160) and any degenerates thereof, and the human glucagon receptor protein as shown in SEQ ID NO:6 (also shown and identified in GenBank GI number: 4503947; Accession number: NP_000151) or to any deriviatives, variants, or active fragments of these sequences.

Definitions

The term "gene" refers to (a) a gene containing at least one of the DNA sequences disclosed herein; (b) any DNA sequence that encodes the amino acid sequence encoded by the DNA sequences disclosed herein; and/or (c) any DNA sequence that hybridizes to the complement of the coding sequences disclosed herein. Preferably, the term includes coding as well as noncoding regions and, preferably, includes all sequences necessary for normal gene expression including promoters, enhancers and other regulatory sequences.

The terms "polynucleotide" and "nucleic acid molecule" are used interchangeably to refer to polymeric forms of nucleotides of any length. The polynucleotides may contain deoxyribonucleotides, ribonucleotides and/or their analogs. Nucleotides may have any three-dimensional structure, and may perform any function, known or unknown. The term "polynucleotide" includes single-, double-stranded and triple helical molecules. "Oligonucleotide" refers to polynucleotides of between 5 and about 100 nucleotides of single- or double-stranded DNA. Oligonucleotides are also known as oligomers or oligos and may be isolated from genes, or chemically synthesized by methods known in the art. A "primer" refers to an oligonucleotide, usually single-stranded, that provides a 3'-hydroxyl end for the initiation of enzyme-mediated nucleic acid synthesis. The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A nucleic acid molecule may also comprise modified nucleic acid molecules, such as methylated nucleic acid molecules and nucleic acid molecule analogs. Analogs of purines and pyrimidines are known in the art, and include, but are not limited to, aziridinycytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5-pentylnyluracil and 2,6-diaminopurine. The use of uracil as a substitute for thymine in a deoxyribonucleic acid is also considered an analogous form of pyrimidine.

A "fragment" of a polynucleotide is a polynucleotide comprised of at least 9 contiguous nucleotides, preferably at least 15 contiguous nucleotides and more preferably at least 45 nucleotides, of coding or non-coding sequences.

The term "gene targeting" refers to a type of homologous recombination that occurs when a fragment of genomic DNA is introduced into a mammalian cell and that fragment locates and recombines with endogenous homologous sequences.

The term "homologous recombination" refers to the exchange of DNA fragments between two DNA molecules or chromatids at the site of homologous nucleotide sequences.

The term "homologous" as used herein denotes a characteristic of a DNA sequence having at least about 70 percent sequence identity as compared to a reference sequence, typically at least about 85 percent sequence identity, preferably at least about 95 percent sequence identity, and more preferably about 98 percent sequence identity, and most preferably about 100 percent sequence identity as compared to a reference sequence. Homology can be determined using, for example, a "BLASTN" algorithm. It is understood that homologous sequences can accommodate insertions, deletions and substitutions in the nucleotide sequence. Thus, linear sequences of nucleotides can be essentially identical even if some of the nucleotide residues do not precisely correspond or align. The reference sequence may be a subset of a larger sequence, such as a portion of a gene or flanking sequence, or a repetitive portion of a chromosome.

As used herein, a "variant" of a glucagon receptor is defined as an amino acid sequence that is different by one or more amino acid substitutions. The variant may have "conservative" changes, wherein a substituted amino acid has similar structural or chemical properties, e.g., replacement of a leucine with isoleucine. More rarely, a variant may have "nonconservative" changes, e.g., replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "active fragment" refers to a fragment of a glucagon receptor that is biologically or immunologically active. The term "biologically active" refers to a glucagon receptor having structural, regulatory or biochemical functions of the naturally occurring glucagon receptor. Likewise, "immunologically active" defines the capability of the natural, recombinant or synthetic glucagon receptor, or any oligopeptide thereof, to induce a specific immune response in appropriate animals or cells and to bind with specific antibodies.

The term "derivative", as used herein, refers to the chemical modification of a nucleic acid sequence encoding a glucagon receptor or the encoded glucagon receptor. An example of such modifications would be replacement of hydrogen by an alkyl, acyl, or amino group. A nucleic acid derivative would encode a polypeptide which retains essential biological characteristics of a natural glucagon receptor.

The term "target gene" (alternatively referred to as "target gene sequence" or "target DNA sequence" or "target sequence") refers to any nucleic acid molecule, polynucleotide, or gene to be modified by homologous recombination. The target sequence includes an intact gene, an exon or intron, a regulatory sequence or any region between genes. The target gene may comprise a portion of a particular gene or genetic locus in the individual's genomic DNA. As provided herein, the target gene of the present invention comprises the glucagon receptor gene as identified and shown in SEQ ID NO: 1 or as identified and shown in Genbank Accession No.: L38613; GI No.: 603463 or to any derivatives, homologues, mutants or fragments of these sequences. In one aspect, the glucagon receptor gene encodes the glucagon receptor comprising the amino acid sequence identified herein as SEQ ID NO:2 or as identified and shown in Genbank Accession No. AAA88244; GI No.: 603464 or any derivatives, homologues, mutants or fragments of these sequences.

"Disruption" of a glucagon receptor gene occurs when a fragment of genomic DNA locates and recombines with an endogenous homologous sequence. These sequence disruptions or modifications may include insertions, missense, frameshift, deletion, or substitutions, or replacements of DNA sequence, or any combination thereof. Insertions include the insertion of entire genes, which may be of animal, plant, fungal, insect, prokaryotic, or viral origin. Disruption, for example, can alter or replace a promoter, enhancer, or splice site of a glucagon receptor gene, and can alter the normal gene product by inhibiting its production partially or completely or by enhancing the normal gene product's activity. In a preferred embodiment, the disruption is a null disruption, wherein there is no significant expression of the glucagon receptor gene.

The term "transgenic cell" refers to a cell containing within its genome a glucagon receptor gene that has been disrupted, modified, altered, or replaced completely or partially by the method of gene targeting.

The term "transgenic animal" refers to an animal that contains within its genome a specific gene that has been disrupted or otherwise modified or mutated by the method of gene targeting. "Transgenic animal" includes both the heterozygous animal (i.e., one defective allele and one wild-type allele) and the homozygous animal (i.e., two defective alleles).

As used herein, the terms "selectable marker" and "positive selection marker" refer to a gene encoding a product that enables only the cells that carry the gene to survive and/or grow under certain conditions. For example, plant and animal cells that express the introduced neomycin resistance (Neo$^r$) gene are resistant to the compound G418. Cells that do not carry the Neo$^r$ gene marker are killed by G418. Other positive selection markers are known to or are within the purview of those of ordinary skill in the art.

A "host cell" includes an individual cell or cell culture that can be or has been a recipient for vector(s) or for incorporation of nucleic acid molecules and/or proteins. Host cells include progeny of a single host cell, and the progeny may not necessarily be completely identical (in morphology or in total DNA complement) to the original parent due to natural, accidental, or deliberate mutation. A host cell includes cells transfected with the constructs of the present invention.

The term "modulates" as used herein refers to the decrease, inhibition, reduction, increase or enhancement of glucagon receptor gene function, expression, activity, or alternatively a phenotype associated with a disruption in a glucagon receptor gene.

The term "ameliorates" refers to a decrease, reduction or elimination of a condition, disease, disorder, or phenotype, including an abnormality or symptom associated with a disruption in a glucagon receptor gene.

The term "abnormality" refers to any disease, disorder, condition, or phenotype in which a disruption of a glucagon receptor gene is implicated, including pathological conditions and behavioral observations.

BRIEF DESCRIPTION OF THE DRAWINGS

FIG. 1A shows the polynucleotide sequence for a murine glucagon receptor gene (SEQ ID NO: 1). FIG. 1B shows the amino acid sequence for the murine glucagon receptor (SEQ ID NO:2).

FIGS. 2A–2B show the location of the disrupted portion of the glucagon receptor gene, as well as the nucleotide sequences flanking the Neo$^r$ insert in the targeting construct.

FIG. 2B shows the sequences identified as SEQ ID NO:3 and SEQ ID NO:4, which were used as the 5' and 3' targeting arms (including the homologous sequences) in the glucagon receptor targeting construct, respectively.

FIG. 3A shows the polynucleotide sequence for a human glucagon receptor gene (SEQ ID NO:5).

FIG. 3B shows the amino acid sequence for the human glucagon receptor (SEQ ID NO:6).

DETAILED DESCRIPTION OF THE INVENTION

Figure 2B:
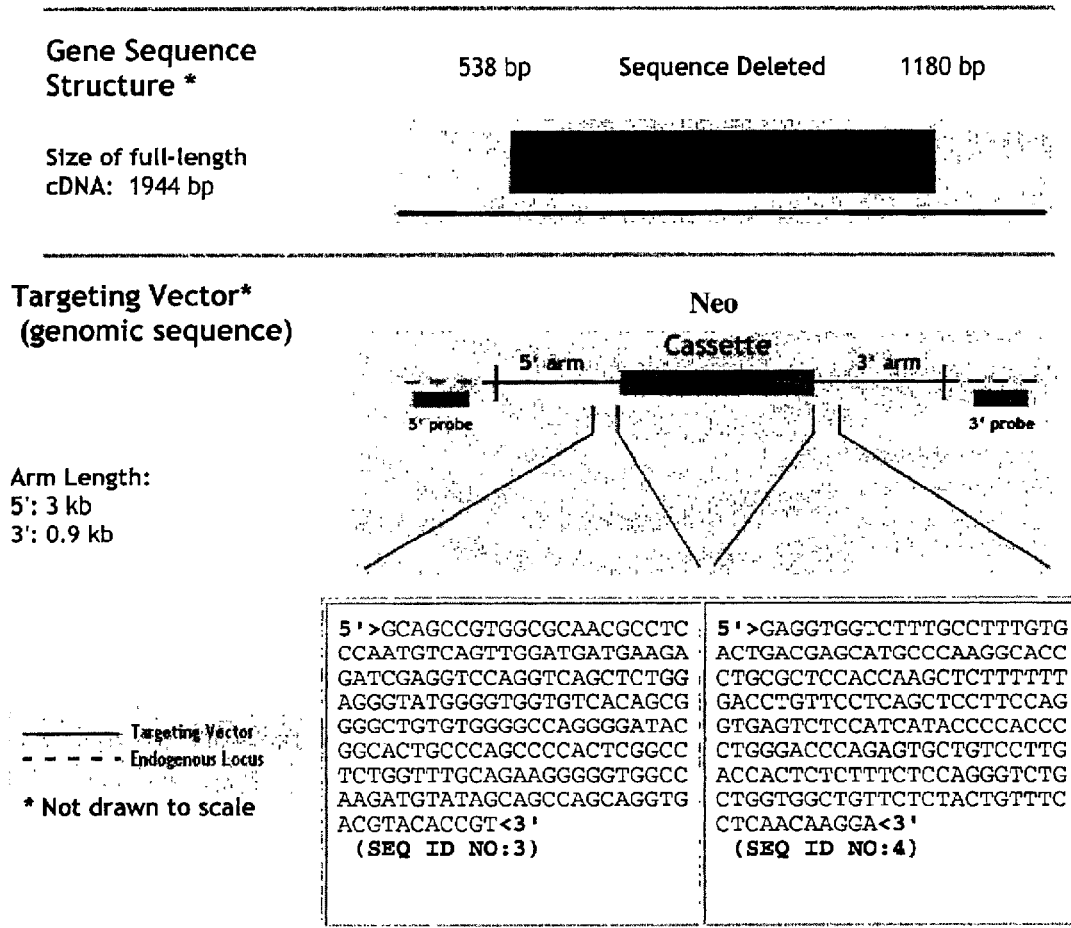

The invention is based, in part, on the evaluation of the expression and role of genes and gene expression products, primarily those associated with a glucagon receptor gene. Among other uses or applications, the invention permits the definition of disease pathways and the identification of diagnostically and therapeutically useful targets. For example, genes that are mutated or down-regulated under disease conditions may be involved in causing or exacerbating the disease condition. Treatments directed at up-regulating the activity of such genes or treatments that involve alternate pathways, may ameliorate the disease condition.

Generation of Targeting Construct

The targeting construct of the present invention may be produced using standard methods known in the art. (see, e.g., Sambrook, et al., 1989, *Molecular Cloning: A Laboratory Manual*, Second Edition, Cold Spring Harbor Laboratory Press, Cold Spring Harbor, N.Y.; E. N. Glover (eds.), 1985, DNA Cloning: *A Practical Approach*, Volumes I and II; M. J. Gait (ed.), 1984, *Oligonucleotide Synthesis*; B. D. Hames & S. J. Higgins (eds.), 1985, Nucleic Acid Hybridization; B. D. Hames & S. J. Higgins (eds.), 1984, *Transcription and Translation*; R. I. Freshney (ed.), 1986, Animal Cell Culture; Immobilized Cells and Enzymes, IRL Press, 1986; B. Perbal, 1984, A Practical Guide To Molecular Cloning; F. M. Ausubel et al., 1994, *Current Protocols in Molecular Biology*, John Wiley & Sons, Inc.). For example, the targeting construct may be prepared in accordance with conventional ways, where sequences may be synthesized, isolated from natural sources, manipulated, cloned, ligated, subjected to in vitro mutagenesis, primer repair, or the like. At various stages, the joined sequences may be cloned, and analyzed by restriction analysis, sequencing, or the like.

The targeting DNA can be constructed using techniques well known in the art. For example, the targeting DNA may be produced by chemical synthesis of oligonucleotides, nick-translation of a double-stranded DNA template, polymerase chain-reaction amplification of a sequence (or ligase chain reaction amplification), purification of prokaryotic or target cloning vectors harboring a sequence of interest (e.g., a cloned cDNA or genomic DNA, synthetic DNA or from any of the aforementioned combination) such as plasmids, phagemids, YACs, cosmids, bacteriophage DNA, other viral DNA or replication intermediates, or purified restriction fragments thereof, as well as other sources of single and double-stranded polynucleotides having a desired nucleotide sequence. Moreover, the length of homology may be selected using known methods in the art. For example, selection may be based on the sequence composition and complexity of the predetermined endogenous target DNA sequence(s).

The targeting construct of the present invention typically comprises a first sequence homologous to a portion or region of the glucagon receptor gene and a second sequence homologous to a second portion or region of the glucagon receptor gene. The targeting construct may further comprise a positive selection marker, which is preferably positioned in between the first and the second homologous sequences. The positive selection marker may be operatively linked to a promoter and a polyadenylation signal.

Other regulatory sequences known in the art may be incorporated into the targeting construct to disrupt or control expression of a particular gene in a specific cell type. In addition, the targeting construct may also include a sequence coding for a screening marker, for example, green fluorescent protein (GFP), or another modified fluorescent protein.

Although the size of the homologous sequence is not critical and can range from as few as about 15-20 base pairs to as many as 100 kb, preferably each fragment is greater than about 1 kb in length, more preferably between about 1 and about 10 kb, and even more preferably between about 1 and about 5 kb. One of skill in the art will recognize that although larger fragments may increase the number of homologous recombination events in ES cells, larger fragments will also be more difficult to clone.

In a preferred embodiment of the present invention, the targeting construct is prepared directly from a plasmid genomic library using the methods described in pending U.S. patent application Ser. No. 08/971,310, filed Nov. 17, 1997, the disclosure of which is incorporated herein in its entirety. Generally, a sequence of interest is identified and isolated from a plasmid library in a single step using, for example, long-range PCR. Following isolation of this sequence, a second polynucleotide that will disrupt the target sequence can be readily inserted between two regions encoding the sequence of interest. In accordance with this aspect, the construct is generated in two steps by (1) amplifying (for example, using long-range PCR) sequences homologous to the target sequence, and (2) inserting another polynucleotide (for example a selectable marker) into the PCR product so that it is flanked by the homologous sequences. Typically, the vector is a plasmid from a plasmid genomic library. The completed construct is also typically a circular plasmid.

In another embodiment, the targeting construct is designed in accordance with the regulated positive selection method described in U.S. patent application Ser. No. 09/954,483, filed Sep. 17, 2000, the disclosure of which is incorporated herein in its entirety. The targeting construct is designed to include a PGK-neo fusion gene having two lacO sites, positioned in the PGK promoter and an NLS-lacl gene comprising a lac repressor fused to sequences encoding the NLS from the SV40 T antigen.

In another embodiment, the targeting construct may contain more than one selectable maker gene, including a negative selectable marker, such as the herpes simplex virus tk (HSV-tk) gene. The negative selectable marker may be operatively linked to a promoter and a polyadenylation signal. (see, e.g., U.S. Pat. Nos. 5,464,764; 5,487,992; 5,627,059; and 5,631,153).

Generation of Cells and Confirmation of Homologous Recombination Events

Once an appropriate targeting construct has been prepared, the targeting construct may be introduced into an appropriate host cell using any method known in the art. Various techniques may be employed in the present invention, including, for example: pronuclear microinjection; retrovirus mediated gene transfer into germ lines; gene targeting in embryonic stem cells; electroporation of embryos; sperm-mediated gene transfer; and calcium phosphate/DNA co-precipitates, microinjection of DNA into the nucleus, bacterial protoplast fusion with intact cells, transfection, polycations, e.g., polybrene, polyomithine, etc., or the like (see, e.g., U.S. Pat. No. 4,873,191; Van der Putten, et al., 1985, *Proc. Natl. Acad. Sci.*, USA 82:6148–6152; Thompson, et al., 1989, *Cell* 56:313–321; Lo, 1983, *Mol Cell. Biol.* 3:1803–1814; Lavitrano, et al., 1989, *Cell,* 57:717–723). Various techniques for transforming mammalian cells are known in the art. (see, e.g., Gordon, 1989, *Intl. Rev. Cytol.,* 115:171–229; Keown et al., 1989, *Methods in Enzymology*; Keown et al., 1990, *Methods and Enzymology*, Vol. 185, pp. 527–537; Mansour et al., 1988, *Nature,* 336:348–352).

In a preferred aspect of the present invention, the targeting construct is introduced into host cells by electroporation. In this process, electrical impulses of high field strength reversibly permeabilize biomembranes allowing the introduction of the construct. The pores created during electroporation permit the uptake of macromolecules such as DNA. (see, e.g., Potter, H., et al., 1984, *Proc. Nat'l. Acad. Sci. U.S.A.* 81:7161–7165).

Any cell type capable of homologous recombination may be used in the practice of the present invention. Examples of such target cells include cells derived from vertebrates including mammals such as humans, bovine species, ovine species, murine species, simian species, and ether eucaryotic organisms such as filamentous fungi, and higher multicellular organisms such as plants.

Preferred cell types include embryonic stem (ES) cells, which are typically obtained from pre-implantation embryos cultured in vitro. (see, e.g., Evans, M. J., et al., 1981, *Nature* 292:154–156; Bradley, M. O., et al., 1984, *Nature* 309:255–258; Gossler et al., 1986, *Proc. Natl. Acad. Sci. USA* 83:9065–9069; and Robertson, et al., 1986, *Nature* 322:445–448). The ES cells are cultured and prepared for introduction of the targeting construct using methods well known to the skilled artisan. (see, e.g., Robertson, E. J. ed. "Teratocarcinomas and Embryonic Stem Cells, a Practical Approach", IRL Press, Washington D.C., 1987; Bradley et al., 1986, *Current Topics in Devel. Biol.* 20:357–371; by Hogan et al., in "Manipulating the Mouse Embryo": A Laboratory Manual, Cold Spring Harbor Laboratory Press, Cold Spring Harbor N.Y., 1986; Thomas et al., 1987, *Cell* 51:503; Koller et al., 1991, *Proc. Natl. Acad. Sci. USA*, 88:10730; Dorin et al., 1992, *Transgenic Res.* 1:101; and Veis et al., 1993, *Cell* 75:229). The ES cells that will be inserted with the targeting construct are derived from an embryo or blastocyst of the same species as the developing embryo into which they are to be introduced. ES cells are typically selected for their ability to integrate into the inner cell mass and contribute to the germ line of an individual when introduced into the mammal in an embryo at the blastocyst stage of development. Thus, any ES cell line having this capability is suitable for use in the practice of the present invention.

The present invention may also be used to knock out or otherwise modify or disrupt genes in other cell types, such as stem cells. By way of example, stem cells may be myeloid, lymphoid, or neural progenitor and precursor cells. These cells comprising a disruption of a gene may be particularly useful in the study of glucagon receptor gene function in individual developmental pathways. Stem cells may be derived from any vertebrate species, such as mouse, rat, dog, cat, pig, rabbit, human, non-human primates and the like.

After the targeting construct has been introduced into cells, the cells in which successful gene targeting has occurred are identified. Insertion of the targeting construct into the targeted gene is typically detected by identifying cells for expression of the marker gene. In a preferred embodiment, the cells transformed with the targeting construct of the present invention are subjected to treatment with an appropriate agent that selects against cells not expressing the selectable marker. Only those cells expressing the selectable marker gene survive and/or grow under certain conditions. For example, cells that express the introduced neomycin resistance gene are resistant to the compound G418, while cells that do not express the neo gene marker are killed by G418. If the targeting construct also comprises a screening marker such as GFP, homologous recombination can be identified through screening cell colonies under a fluorescent light. Cells that have undergone homologous recombination will have deleted the GFP gene and will not fluoresce.

If a regulated positive selection method is used in identifying homologous recombination events, the targeting construct is designed so that the expression of the selectable marker gene is regulated in a manner such that expression is inhibited following random integration but is permitted (derepressed) following homologous recombination. More particularly, the transfected cells are screened for expression of the neo gene, which requires that (1) the cell was successfully electroporated, and (2) lac repressor inhibition of neo transcription was relieved by homologous recombination. This method allows for the identification of transfected cells and homologous recombinants to occur in one step with the addition of a single drug.

Alternatively, a positive-negative selection technique may be used to select homologous recombinants. This technique involves a process in which a first drug is added to the cell population, for example, a neomycin-like drug to select for growth of transfected cells, i.e. positive selection. A second drug, such as FIAU is subsequently added to kill cells that express the negative selection marker, i.e. negative selection. Cells that contain and express the negative selection marker are killed by a selecting agent, whereas cells that do not contain and express the negative selection marker survive. For example, cells with non-homologous insertion of the construct express HSV thymidine kinase and therefore are sensitive to the herpes drugs such as gancyclovir (GANC) or FIAU (1-(2-deoxy 2-fluoro-B-D-arabinofluranosyl)-5-iodouracil). (see, e.g., Mansour et al., *Nature* 336:348–352: (1988); Capecchi, *Science* 244:1288–1292, (1989); Capecchi, *Trends in Genet.* 5:70–76 (1989)).

Successful recombination may be identified by analyzing the DNA of the selected cells to confirm homologous recombination. Various techniques known in the art, such as PCR and/or Southern analysis may be used to confirm homologous recombination events.

Homologous recombination may also be used to disrupt genes in stem cells, and other cell types, which are not totipotent embryonic stem cells. By way of example, stem cells may be myeloid, lymphoid, or neural progenitor and precursor cells. Such transgenic cells may be particularly useful in the study of glucagon receptor gene function in individual developmental pathways. Stem cells may be derived from any vertebrate species, such as mouse, rat, dog, cat, pig, rabbit, human, non-human primates and the like.

In cells that are not totipotent, it may be desirable to knock out both copies of the target using methods that are known in the art. For example, cells comprising homologous recombination at a target locus that have been selected for expression of a positive selection marker (e.g., Neor) and screened for non-random integration, can be further selected for multiple copies of the selectable marker gene by exposure to elevated levels of the selective agent (e.g., G418). The cells are then analyzed for homozygosity at the target locus. Alternatively, a second construct can be generated with a different positive selection marker inserted between the two homologous sequences. The two constructs can be introduced into the cell either sequentially or simultaneously, followed by appropriate selection for each of the positive marker genes. The final cell is screened for homologous recombination of both alleles of the target.

Production of Transgenic Animals

Selected cells are then injected into a blastocyst (or other stage of development suitable for the purposes of creating a viable animal, such as, for example, a morula) of an animal (e.g., a mouse) to form chimeras (see e.g., Bradley, A. in *Teratocarcinomas and Embryonic Stem Cells: A Practical Approach*, E. J. Robertson, ed., IRL, Oxford, pp. 113–152 (1987)). Alternatively, selected ES cells can be allowed to aggregate with dissociated mouse embryo cells to form the aggregation chimera. A chimeric embryo can then be implanted into a suitable pseudopregnant female foster animal and the embryo brought to term. Chimeric progeny harboring the homologously recombined DNA in their germ cells can be used to breed animals in which all cells of the animal contain the homologously recombined DNA. In one embodiment, chimeric progeny mice are used to generate a mouse with a heterozygous disruption in the glucagon receptor gene. Heterozygous transgenic mice can then be mated. It is well known in the art that typically ¼ of the offspring of such matings will have a homozygous disruption in the glucagon receptor gene.

The heterozygous and homozygous transgenic mice can then be compared to normal, wild-type mice to determine whether disruption of the glucagon receptor gene causes phenotypic changes, especially pathological changes. For example, heterozygous and homozygous mice may be evaluated for phenotypic changes by physical examination, necropsy, histology, clinical chemistry, complete blood count, body weight, organ weights, and cytological evaluation of bone marrow. Phenotypic changes may also comprise behavioral modifications or abnormalities.

In one embodiment, the phenotype (or phenotypic change) associated with a disruption in the glucagon receptor gene is placed into or stored in a database. Preferably, the database includes: (i) genotypic data (e.g., identification of the disrupted gene) and (ii) phenotypic data (e.g., phenotype (s) resulting from the gene disruption) associated with the genotypic data. The database is preferably electronic. In addition, the database is preferably combined with a search tool so that the database is searchable.

Conditional Transgenic Animals

The present invention further contemplates conditional transgenic or knockout animals, such as those produced using recombination methods. Bacteriophage P1 Cre recombinase and flp recombinase from yeast plasmids are two non-limiting examples of site-specific DNA recombinase enzymes that cleave DNA at specific target sites (lox P sites for cre recombinase and frt sites for flp recombinase) and catalyze a ligation of this DNA to a second cleaved site. A large number of suitable alternative site-specific recombinases have been described, and their genes can be used in accordance with the method of the present invention. Such recombinases include the Int recombinase of bacteriophage λ (with or without Xis) (Weisberg, R. et al., in *Lambda II*, (Hendrix, R., et al., Eds.), Cold Spring Harbor Press, Cold Spring Harbor, N.Y., pp. 211–50 (1983), herein incorporated by reference); TpnI and the β-lactamase transposons (Mercier, et al., *J. Bacteriol.*, 172:3745–57 (1990)); the Tn3 resolvase (Flanagan & Fennewald *J. Molec. Biol.*, 206:295–304 (1989); Stark, et al., *Cell*, 58:779–90 (1989)); the yeast recombinases (Matsuzaki, et al., *J. Bacteriol.*, 172:610–18 (1990)); the *B. subtilis* SpoIVC recombinase (Sato, et al., *J. Bacteriol.* 172:1092–98 (1990)); the Flp recombinase (Schwartz & Sadowski, *J. Molec.Biol.*, 205:647–658 (1989); Parsons, et al., *J. Biol. Chem.*, 265:4527–33 (1990); Golic & Lindquist, *Cell*, 59:499–509 (1989); Amin, et al., *J. Molec. Biol.*, 214:55–72 (1990)); the Hin recombinase (Glasgow, et al., *J. Biol. Chem.*, 264:10072–82 (1989)); immunoglobulin recombinases (Malynn, et al., *Cell*, 54:453–460 (1988)); and the Cin recombinase (Haffter & Bickle, *EMBO J.*, 7:3991–3996 (1988); Hubner, et al., *J. Molec. Biol.*, 205:493–500 (1989)), all herein incorporated by reference. Such systems are discussed by Echols (*J. Biol. Chem.* 265:14697–14700 (1990)); de Villartay (*Nature*, 335:170–74 (1988)); Craig, (Ann. Rev. *Genet.*, 22:77–105 (1988)); Poyart-Salmeron, et al., (*EMBO J.* 8:2425–33 (1989)); Hunger-Bertling, et al., (*Mol Cell. Biochem.*, 92:107–16 (1990)); and Cregg & Madden (Mol. *Gen. Genet.*, 219:320–23 (1989)), all herein incorporated by reference.

Cre has been purified to homogeneity, and its reaction with the loxP site has been extensively characterized (Abremski & Hess *J. Mol. Biol.* 259:1509–14 (1984), herein incorporated by reference). Cre protein has a molecular weight of 35,000 and can be obtained commercially from New England Nuclear/Du Pont. The cre gene (which encodes the Cre protein) has been cloned and expressed (Abremski, et al., *Cell* 32:1301–11 (1983), herein incorporated by reference). The Cre protein mediates recombination between two loxP sequences (Sternberg, et al., *Cold Spring Harbor Symp. Quant. Biol.* 45:297–309 (1981)), which may be present on the same or different DNA molecule. Because the internal spacer sequence of the loxP site is asymmetrical, two loxP sites can exhibit directionality relative to one another (Hoess & Abremski *Proc. Natl. Acad. Sci. U.S.A.* 81:1026–29 (1984)). Thus, when two sites on the same DNA molecule are in a directly repeated orientation, Cre will excise the DNA between the sites (Abremski, et al., *Cell* 32:1301–11 (1983)). However, if the sites are inverted with respect to each other, the DNA between them is not excised after recombination but is simply inverted. Thus, a circular DNA molecule having two loxP sites in direct orientation will recombine to produce two smaller circles, whereas circular molecules having two loxP sites in an inverted orientation simply invert the DNA sequences flanked by the loxP sites. In addition, recombinase action can result in reciprocal exchange of regions distal to the target site when targets are present on separate DNA molecules.

Recombinases have important application for characterizing gene function in knockout models. When the constructs described herein are used to disrupt glucagon receptor genes, a fusion transcript can be produced when insertion of the positive selection marker occurs downstream (3') of the translation initiation site of the glucagon receptor gene. The fusion transcript could result in some level of protein expression with unknown consequence. It has been suggested that insertion of a positive selection marker gene can affect the expression of nearby genes. These effects may make it difficult to determine gene function after a knockout event since one could not discern whether a given phenotype is associated with the inactivation of a gene, or the transcription of nearby genes. Both potential problems are solved by exploiting recombinase activity. When the positive selection marker is flanked by recombinase sites in the same orientation, the addition of the corresponding recombinase will result in the removal of the positive selection marker. In this way, effects caused by the positive selection marker or expression of fusion transcripts are avoided.

In one embodiment, purified recombinase enzyme is provided to the cell by direct microinjection. In another embodiment, recombinase is expressed from a co-transfected construct or vector in which the recombinase gene is operably linked to a functional promoter. An additional aspect of this embodiment is the use of tissue-specific or inducible recombinase constructs that allow the choice of when and where recombination occurs. One method for practicing the inducible forms of recombinase-mediated recombination involves the use of vectors that use inducible or tissue-specific promoters or other gene regulatory elements to express the desired recombinase activity. The inducible expression elements are preferably operatively positioned to allow the inducible control or activation of expression of the desired recombinase activity. Examples of such inducible promoters or other gene regulatory elements include, but are not limited to, tetracycline, metallothionine, ecdysone, and other steroid-responsive promoters, rapamycin responsive promoters, and the like (No, et al., *Proc. Natl.*

*Acad. Sci. USA,* 93:3346–51 (1996); Furth, et al., *Proc. Natl. Acad. Sci. USA,* 91:9302–6 (1994)). Additional control elements that can be used include promoters requiring specific transcription factors such as viral, promoters. Vectors incorporating such promoters would only express recombinase activity in cells that express the necessary transcription factors.

Models for Disease

The cell- and animal-based systems described herein can be utilized as models for diseases. Animals of any species, including, but not limited to, mice, rats, rabbits, guinea pigs, pigs, micro-pigs, goats, and non-human primates, e.g., baboons, monkeys, and chimpanzees may be used to generate disease animal models. In addition, cells from humans may be used. These systems may be used in a variety of applications. Such assays may be utilized as part of screening strategies designed to identify agents, such as compounds that are capable of ameliorating disease symptoms. Thus, the animal- and cell-based models may be used to identify drugs, pharmaceuticals, therapies and interventions that may be effective in treating disease.

Cell-based systems may be used to identify compounds that may act to ameliorate disease symptoms. For example, such cell systems may be exposed to a compound suspected of exhibiting an ability to ameliorate disease symptoms, at a sufficient concentration and for a time sufficient to elicit such an amelioration of disease symptoms in the exposed cells. After exposure, the cells are examined to determine whether one or more of the disease cellular phenotypes has been altered to resemble a more normal or more wild-type, non-disease phenotype.

In addition, animal-based disease systems, such as those described herein, may be used to identify compounds capable of ameliorating disease symptoms. Such animal models may be used as test substrates for the identification of drugs, pharmaceuticals, therapies, and interventions that may be effective in treating a disease or other phenotypic characteristic of the animal. For example, animal models may be exposed to a compound or agent suspected of exhibiting an ability to ameliorate disease symptoms, at a sufficient concentration and for a time sufficient to elicit such an amelioration of disease symptoms in the exposed animals. The response of the animals to the exposure may be monitored by assessing the reversal of disorders associated with the disease. Exposure may involve treating mother animals during gestation of the model animals described herein, thereby exposing embryos or fetuses to the compound or agent that may prevent or ameliorate the disease or phenotype. Neonatal, juvenile, and adult animals can also be exposed.

More particularly, using the animal models of the invention, methods of identifying agents are provided, in which such agents can be identified on the basis of their ability to affect at least one phenotype associated with a disruption in a glucagon receptor gene. In one embodiment, the present invention provides a method of identifying agents having an effect on glucagon receptor gene expression or function. The method includes measuring a physiological response of the animal, for example, to the agent and comparing the physiological response of such animal to a control animal, wherein the physiological response of the animal comprising a disruption in a glucagon receptor gene as compared to the control animal indicates the specificity of the agent. A "physiological response" is any biological or physical parameter of an animal that can be measured. Molecular assays (e.g., gene transcription, protein production and degradation rates), physical parameters (e.g., exercise physiology tests, measurement of various parameters of respiration, measurement of heart rate or blood pressure, and measurement of bleeding time), behavioral testing, and cellular assays (e.g.,. immunohistochemical assays of cell surface markers, or the ability of cells to aggregate or proliferate) can be used to assess a physiological response.

The transgenic animals and cells of the present invention may be utilized as models for diseases, disorders, or conditions associated with phenotypes relating to a disruption in a glucagon receptor gene. In one aspect, the phenotype associated with a homozygous or heterozygous disruption in a gene encoding a glucagon receptor is an abnormality in Islet of Langerhans cells of the pancreas, e.g. hyperplasia, hypertrophy, increased cytoplasmic vacuolization and granularity and/or adenomas of the islet cells, as described in Example 3 set forth below. In another aspect, the phenotype associated with a disruption in a gene encoding a glucagon receptor is one or more of the following abnormalities: reduced body weight and/or organ weight, abnormal body shape (e.g. dwarfism), decreased body fat percentage, decreased serum glucose levels, and infertility (see Example 3 below). In another aspect, the transgenic animals and cells of the present invention exhibit an increased tolerance to glucose as compared to wild-type mice. As set forth in the Example 4 below, the transgenic animals or cells of the present invention may serve as models for glucose metabolism. Alternatively, overexpression of the glucagon receptor in a transgenic model may serve as a model for diabetes, in particular, type II diabetes.

The present invention provides a unique animal model for testing and developing new treatments relating to the behavioral phenotypes. Analysis of the behavioral phenotype allows for the development of an animal model useful for testing, for instance, the efficacy of proposed genetic and pharmacological therapies for human genetic diseases, such as neurological, neuropsychological, or psychotic illnesses.

A statistical analysis of the various behaviors measured can be carried out using any conventional statistical program routinely used by those skilled in the art (such as, for example, "Analysis of Variance" or ANOVA). A "p" value of about 0.05 or less is generally considered to be statistically significant, although slightly higher p values may still be indicative of statistically significant differences. To statistically analyze abnormal behavior, a comparison is made between the behavior of a transgenic animal (or a group thereof) to the behavior of a wild-type mouse (or a group thereof), typically under certain prescribed conditions. "Abnormal behavior" as used herein refers to behavior exhibited by an animal having a disruption in the glucagon receptor gene, e.g. transgenic animal, which differs from an animal without a disruption in the glucagon receptor gene, e.g. wild-type mouse. Abnormal behavior consists of any number of standard behaviors that can be objectively measured (or observed) and compared. In the case of comparison, it is preferred that the change be statistically significant to confirm that there is indeed a meaningful behavioral difference between the knockout animal and the wild-type control animal. Examples of behaviors that may be measured or observed include, but are not limited to, ataxia, rapid limb movement, eye movement, breathing, motor activity, cognition, emotional behaviors, social behaviors, hyperactivity, hypersensitivity, anxiety, impaired learning, abnormal reward behavior, and abnormal social interaction, such as aggression.

A series of tests may be used to measure the behavioral phenotype of the animal models of the present invention, including neurological and neuropsychological tests to identify abnormal behavior. These tests may be used to measure abnormal behavior relating to, for example, learning and memory, eating, pain, aggression, sexual reproduction, anxiety, depression, schizophrenia, and drug abuse. (see, e.g., Crawley & Paylor, *Hormones and Behavior* 31:197–211 (1997)).

The social interaction test involves exposing a mouse to other animals in a variety of settings. The social behaviors of the animals (e.g., touching, climbing, sniffing, and mating) are subsequently evaluated. Differences in behaviors can then be statistically analyzed and compared (see, e.g., S. E. File, et al., *Pharmacol. Bioch. Behav.* 22:941–944 (1985); R. R. Holson, *Phys. Behav.* 37:239–247 (1986)). Examplary behavioral tests include the following.

The mouse startle response test typically involves exposing the animal to a sensory (typically auditory) stimulus and measuring the startle response of the animal (see, e.g., M. A. Geyer, et al., *Brain Res. Bull.* 25:485–498 (1990); Paylor and Crawley, *Psychopharmacology* 132:169–180 (1997)). A pre-pulse inhibition test can also be used, in which the percent inhibition (from a normal startle response) is measured by "cueing" the animal first with a brief low-intensity pre-pulse prior to the startle pulse.

The electric shock test generally involves exposure to an electrified surface and measurement of subsequent behaviors such as, for example, motor activity, learning, social behaviors. The behaviors are measured and statistically analyzed using standard statistical tests. (see, e.g., G. J. Kant, et al., *Pharm. Bioch. Behav.* 20:793–797 (1984); N. J. Leidenheimer, et al., *Pharmacol. Bioch. Behav.* 30:351–355 (1988)).

The tail-pinch or immobilization test involves applying pressure to the tail of the animal and/or restraining the animal's movements. Motor activity, social behavior, and cognitive behavior are examples of the areas that are measured. (see, e.g., M. Bertolucci D'Angic, et al., *Neurochem.* 55:1208–1214 (1990)).

The novelty test generally comprises exposure to a novel environment and/or novel objects. The animal's motor behavior in the novel environment and/or around the novel object are measured and statistically analyzed. (see, e.g., D. K. Reinstein, et al., *Pharm. Bioch. Behav.* 17:193–202 (1982); B. Poucet, *Behav. Neurosci.* 103:1009–10016 (1989); R. R. Holson, et al., *Phys. Behav.* 37:231–238 (1986)). This test may be used to detect visual processing deficiencies or defects.

The learned helplessness test involves exposure to stresses, for example, noxious stimuli, which cannot be affected by the animal's behavior. The animal's behavior can be statistically analyzed using various standard statistical tests. (see, e.g., A. Leshner, et al., *Behav. Neural Biol.* 26:497–501 (1979)).

Alternatively, a tail suspension test may be used, in which the "immobile" time of the mouse is measured when suspended "upside-down" by its tail. This is a measure of whether the animal struggles, an indicator of depression. In humans, depression is believed to result from feelings of a lack of control over one's life or situation. It is believed that a depressive state can be elicited in animals by repeatedly subjecting them to aversive situations over which they have no control. A condition of "learned helplessness" is eventually reached, in which the animal will stop trying to change its circumstances and simply accept its fate. Animals that stop struggling sooner are believed to be more prone to depression. Studies have shown that the administration of certain antidepressant drugs prior to testing increases the amount of time that animals struggle before giving up.

The Morris water-maze test comprises learning spatial orientations in water and subsequently measuring the animal's behaviors, such as, for example, by counting the number of incorrect choices. The behaviors measured are statistically analyzed using standard statistical tests. (see, e.g., E. M. Spruijt, et al., *Brain Res.* 527:192–197 (1990)).

Alternatively, a Y-shaped maze may be used (see, e.g., McFarland, D. J., *Pharmacology, Biochemistry and Behavior* 32:723–726 (1989); Dellu, F., et al., *Neurobiology of Learning and Memory* 73:31–48 (2000)). The Y-maze is generally believed to be a test of cognitive ability. The dimensions of each arm of the Y-maze can be, for example, approximately 40 cm×8 cm×20 cm, although other dimensions may be used. Each arm can also have, for example, sixteen equally spaced photobeams to automatically detect movement within the arms. At least two different tests can be performed using such a Y-maze. In a continuous Y-maze paradigm, mice are allowed to explore all three arms of a Y-maze for, e.g., approximately 10 minutes. The animals are continuously tracked using photobeam detection grids, and the data can be used to measure spontaneous alteration and positive bias behavior. Spontaneous alteration refers to the natural tendency of a "normal" animal to visit the least familiar arm of a maze. An alternation is scored when the animal makes two consecutive turns in the same direction, thus representing a sequence of visits to the least recently entered arm of the maze. Position bias determines egocentrically defined responses by measuring the animal's tendency to favor turning in one direction over another. Therefore, the test can detect differences in an animal's ability to navigate on the basis of allocentric or egocentric mechanisms. The two-trial Y-maze memory test measures response to novelty and spatial memory based on a free-choice exploration paradigm. During the first trial (acquisition), the animals are allowed to freely visit two arms of the Y-maze for, e.g., approximately 15 minutes. The third arm is blocked off during this trial. The second trial (retrieval) is performed after an intertrial interval of, e.g., approximately 2 hours. During the retrieval trial, the blocked arm is opened and the animal is allowed access to all three arms for, e.g., approximately 5 minutes. Data are collected during the retrieval trial and analyzed for the number and duration of visits to each arm. Because the three arms of the maze are virtually identical, discrimination between novelty and familiarity is dependent on "environmental" spatial cues around the room relative to the position of each arm. Changes in arm entry and duration of time spent in the novel arm in a transgenic animal model may be indicative of a role of that gene in mediating novelty and recognition processes.

The passive avoidance or shuttle box test generally involves exposure to two or more environments, one of which is noxious, providing a choice to be learned by the animal. Behavioral measures include, for example, response latency, number of correct responses, and consistency of response. (see, e.g., R. Ader, et al., *Psychon. Sci.* 26:125–128 (1972); R. R. Holson, *Phys. Behav.* 37:221–230 (1986)). Alternatively, a zero-maze can be used. In a zero-maze, the animals can, for example, be placed in a closed quadrant of an elevated annular platform having, e.g., 2 open and 2 closed quadrants, and are allowed to explore for approximately 5 minutes. This paradigm exploits an approach-avoidance conflict between normal exploratory activity and an aversion to open spaces in rodents. This test measures anxiety levels and can be used to evaluate the effectiveness of anti-anxiolytic drugs. The time spent in open quadrants versus closed quadrants may be recorded automatically, with, for example, the placement of photobeams at each transition site.

The food avoidance test involves exposure to novel food and objectively measuring, for example, food intake and intake latency. The behaviors measured are statistically analyzed using standard statistical tests. (see, e.g., B. A. Campbell, et al., *J. Comp. Physiol. Psychol.* 67:15–22 (1969)).

The elevated plus-maze test comprises exposure to a maze, without sides, on a platform, the animal's behavior is objectively measured by counting the number of maze entries and maze learning. The behavior is statistically analyzed using standard statistical tests. (see, e.g., H. A. Baldwin, et al., *Brain Res. Bull,* 20:603–606 (1988)).

The stimulant-induced hyperactivity test involves injection of stimulant drugs (e.g., amphetamines, cocaine, PCP, and the like), and objectively measuring, for example, motor activity, social interactions, cognitive behavior. The animal's behaviors are statistically analyzed using standard statistical tests. (see, e.g., P. B. S. Clarke, et al., *Psychopharmacology* 96:511–520 (1988); P. Kuczenski, et al., *J. Neuroscience* 11:2703–2712 (1991)).

The self-stimulation test generally comprises providing the mouse with the opportunity to regulate electrical and/or chemical stimuli to its own brain. Behavior is measured by frequency and pattern of self-stimulation. Such behaviors are statistically analyzed using standard statistical tests. (see, e.g., S. Nassif, et al., *Brain Res.,* 332:247–257 (1985); W. L. Isaac, et al., *Behav. Neurosci.* 103:345–355 (1989)).

The reward test involves shaping a variety of behaviors, e.g., motor, cognitive, and social, measuring, for example, rapidity and reliability of behavioral change, and statistically analyzing the behaviors measured. (see, e.g., L. E. Jarrard, et al., Exp. Brain Res. 61:519–530 (1986)).

The DRL (differential reinforcement to low rates of responding) performance test involves exposure to intermittent reward paradigms and measuring the number of proper responses, e.g., lever pressing. Such behavior is statistically analyzed using standard statistical tests. (see, e.g., J. D. Sinden, et al., Behav. Neurosci. 100:320–329 (1986); V. Nalwa, et al., Behav Brain Res. 17:73–76 (1985); and A. J. Nonneman, et al., J. Comp. Physiol. Psych. 95:588–602 (1981)).

The spatial learning test involves exposure to a complex novel environment, measuring the rapidity and extent of spatial learning, and statistically analyzing the behaviors measured. (see, e.g., N. Pitsikas, et al., Pharm. Bioch. Behav. 38:931–934 (1991); B. poucet, et al., Brain Res. 37:269–280 (1990); D. Christie, et al., Brain Res. 37:263–268 (1990); and F. Van Haaren, et al., Behav. Neurosci. 102:481–488 (1988)). Alternatively, an open-field (of) test may be used, in which the greater distance traveled for a given amount of time is a measure of the activity level and anxiety of the animal. When the open field is a novel environment, it is believed that an approach-avoidance situation is created, in which the animal is "torn" between the drive to explore and the drive to protect itself. Because the chamber is lighted and has no places to hide other than the corners, it is expected that a "normal" mouse will spend more time in the corners and around the periphery than it will in the center where there is no place to hide. "Normal" mice will, however, venture into the central regions as they explore more and more of the chamber. It can then be extrapolated that especially anxious mice will spend most of their time in the corners, with relatively little or no exploration of the central region, whereas bold (i.e., less anxious) mice will travel a greater distance, showing little preference for the periphery versus the central region.

The visual, somatosensory and auditory neglect tests generally comprise exposure to a sensory stimulus, objectively measuring, for example, orientating responses, and statistically analyzing the behaviors measured. (see, e.g., J. M. Vargo, et al., Exp. Neurol. 102:199–209 (1988)).

The consummatory behavior test generally comprises feeding and drinking, and objectively measuring quantity of consumption. The behavior measured is statistically analyzed using standard statistical tests. (see, e.g., P. J. Fletcher, et al., Psychopharmacol. 102:301–308 (1990); M. G. Corda, et al.,, Proc. Nat'l Acad. Sci. USA 80:2072–2076 (1983)).

A visual discrimination test can also be used to evaluate the visual processing of an animal. One or two similar objects are placed in an open field and the animal is allowed to explore for about 5–10 minutes. The time spent exploring each object (proximity to, i.e., movement within, e.g., about 3–5 cm of the object is considered exploration of an object) is recorded. The animal is then removed from the open field, and the objects are replaced by a similar object and a novel object. The animal is returned to the open field and the percent time spent exploring the novel object over the old object is measured (again, over about a 5–10 minute span). "Normal" animals will typically spend a higher percentage of time exploring the novel object rather than the old object. If a delay is imposed between sampling and testing, the memory task becomes more hippocampal-dependent. If no delay is imposed, the task is more based on simple visual discrimination. This test can also be used for olfactory discrimination, in which the objects (preferably, simple blocks) can be sprayed or otherwise treated to hold an odor. This test can also be used to determine if the animal can make gustatory discriminations; animals that return to the previously eaten food instead of novel food exhibit gustatory neophobia.

A hot plate analgesia test can be used to evaluate an animal's sensitivity to heat or painful stimuli. For example, a mouse can be placed on an approximately 55° C. hot plate and the mouse's response latency (e.g., time to pick up and lick a hind paw) can be recorded. These responses are not reflexes, but rather "higher" responses requiring cortical involvement. This test may be used to evaluate a nociceptive disorder.

An accelerating rotarod test may be used to measure coordination and balance in mice. Animals can be, for example, placed on a rod that acts like a rotating treadmill (or rolling log). The rotarod can be made to rotate slowly at first and then progressively faster until it reaches a speed of, e.g., approximately 60 rpm. The mice must continually reposition themselves in order to avoid falling off. The animals are preferably tested in at least three trials, a minimum of 20 minutes apart. Those mice that are able to stay on the rod the longest are believed to have better coordination and balance.

A metrazol administration test can be used to screen animals for varying susceptibilities to seizures or similar events. For example, a 5mg/ml solution of metrazol can be infused through the tail vein of a mouse at a rate of, e.g., approximately 0.375 ml/min. The infusion will cause all mice to experience seizures, followed by death. Those mice that enter the seizure stage the soonest are believed to be more prone to seizures. Four distinct physiological stages can be recorded: soon after the start of infusion, the mice will exhibit a noticeable "twitch", followed by a series of seizures, ending in a final tensing of the body known as "tonic extension", which is followed by death.

Glucagon Receptor Gene Products

The present invention further contemplates use of the glucagon receptor gene sequence to produce glucagon receptor gene products. Glucagon receptor gene products may include proteins that represent functionally equivalent gene products. Such an equivalent gene product may contain deletions, additions or substitutions of amino acid residues within the amino acid sequence encoded by the gene sequences described herein, but which result in a silent change, thus producing a functionally equivalent glucagon receptor gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous gene products encoded by the glucagon receptor gene sequences. Alternatively, when utilized as part of an assay, "functionally equivalent" may refer to peptides capable of interacting with other cellular or extracellular molecules in a manner substantially similar to the way in which the corresponding portion of the endogenous gene product would.

Other protein products useful according to the methods of the invention are peptides derived from or based on the glucagon receptor gene produced by recombinant or synthetic means (derived peptides).

Glucagon receptor gene products may be produced by recombinant DNA technology using techniques well known in the art. Thus, methods for preparing the gene polypeptides and peptides of the invention by expressing nucleic acid encoding gene sequences are described herein. Methods that are well known to those skilled in the art can be used to construct expression vectors containing gene protein coding sequences and appropriate transcriptional/translational control signals. These methods include, for example, in vitro recombinant DNA techniques, synthetic techniques and in vivo recombination/genetic recombination (see, e.g., Sambrook, et al., 1989, supra, and Ausubel, et al., 1989, supra). Alternatively, RNA capable of encoding gene protein sequences may be chemically synthesized using, for example, automated synthesizers (see, e.g. Oligonucleotide Synthesis: A Practical Approach, Gait, M. J. ed., IRL Press, Oxford (1984)).

A variety of host-expression vector systems may be utilized to express the gene coding sequences of the invention. Such host-expression systems represent vehicles by which the coding sequences of interest may be produced and subsequently purified, but also represent cells that may, when transformed or transfected with the appropriate nucleotide coding sequences, exhibit the gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing gene protein coding sequences; yeast (e.g. *Saccharomyces, Pichia*) transformed with recombinant yeast expression vectors containing the gene protein coding sequences; insect cell systems infected with recombinant virus expression vectors (e.g., baculovirus) containing the gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing gene protein coding sequences; or mammalian cell systems (e.g. COS, CHO, BHK, 293, 3T3) harboring recombinant expression constructs containing promoters derived from the genome of mammalian cells (e.g., metallothionine promoter) or from mammalian viruses (e.g., the adenovirus late promoter; the vaccinia virus 7.5 K promoter).

In bacterial systems, a number of expression vectors may be advantageously selected depending upon the use intended for the gene protein being expressed. For example, when a large quantity of such a protein is to be produced, for the generation of antibodies or to screen peptide libraries, for example, vectors that direct the expression of high levels of fusion protein products that are readily purified may be desirable. Such vectors include, but are not limited, to the *E. coli* expression vector pUR278 (Ruther et al., *EMBO J.*, 2:1791–94 (1983)), in which the gene protein coding sequence may be ligated individually into the vector in frame with the lac Z coding region so that a fusion protein is produced; pIN vectors (Inouye & Inouye, *Nucleic Acids Res.*, 13:3101–09 (1985); Van Heeke et al., *J. Biol. Chem.*, 264:5503–9 (1989)); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned glucagon receptor gene protein can be released from the GST moiety.

In a preferred embodiment, full length cDNA sequences are appended with in-frame Bam HI sites at the amino terminus and Eco RI sites at the carboxyl terminus using standard PCR methodologies (Innis, et al. (eds) PCR Protocols: A Guide to Methods and Applications, Academic Press, San Diego (1990)) and ligated into the pGEX-2TK vector (Pharmacia, Uppsala, Sweden). The resulting cDNA construct contains a kinase recognition site at the amino terminus for radioactive labeling and glutathione S-transferase sequences at the carboxyl terminus for affinity purification (Nilsson, et al., *EMBO J.*, 4: 1075–80 (1985); Zabeau et al., *EMBO J.*, 1: 1217–24 (1982)).

In an insect system, *Autographa californica* nuclear polyhedrosis virus (AcNPV) is used as a vector to express foreign genes. The virus grows in *Spodoptera frugiperda* cells. The gene coding sequence may be cloned individually into non-essential regions (for example the polyhedrin gene) of the virus and placed under control of an AcNPV promoter (for example the polyhedrin promoter). Successful insertion of gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (see, e.g., Smith, et al., *J. Virol.* 46:584–93 (1983); U.S. Pat. No. 4,745,051).

In mammalian host cells, a number of viral-based expression systems may be utilized. In cases where an adenovirus is used as an expression vector, the gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing gene protein in infected hosts. (e.g., see Logan et al., *Proc. Natl.*

*Acad. Sci. USA*, 81:3655–59 (1984)). Specific initiation signals may also be required for efficient translation of inserted gene coding sequences. These signals include the ATG initiation codon and adjacent sequences. In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter, et al., *Methods in Enzymol.*, 153:516–44 (1987)).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, etc.

For long-term, high-yield production of recombinant proteins, stable expression is preferred. For example, cell lines that stably express the gene protein may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells that stably integrate the plasmid into their chromosomes and grow, to form foci, which in turn can be cloned and expanded into cell lines. This method may advantageously be used to engineer cell lines that express the gene protein. Such engineered cell lines may be particularly useful in screening and evaluation of compounds that affect the endogenous activity of the gene protein.

In a preferred embodiment, timing and/or quantity of expression of the recombinant protein can be controlled using an inducible expression construct. Inducible constructs and systems for inducible expression of recombinant proteins will be well known to those skilled in the art. Examples of such inducible promoters or other gene regulatory elements include, but are not limited to, tetracycline, metallothionine, ecdysone, and other steroid-responsive promoters, rapamycin responsive promoters, and the like (No, et al., *Proc. Natl. Acad. Sci. USA*, 93:3346–51 (1996); Furth, et al., *Proc. Natl. Acad. Sci. USA*, 91:9302–6 (1994)). Additional control elements that can be used include promoters requiring specific transcription factors such as viral, particularly HIV, promoters. In one in embodiment, a Tet inducible gene expression system is utilized. (Gossen et al., *Proc. Natl. Acad. Sci. USA*, 89:5547–51 (1992); Gossen, et al., *Science*, 268:1766–69 (1995)). Tet Expression Systems are based on two regulatory elements derived from the tetracycline-resistance operon of the *E. coli* Tn10 transposon—the tetracycline repressor protein (TetR) and the tetracycline operator sequence (tetO) to which TetR binds. Using such a system, expression of the recombinant protein is placed under the control of the tetO operator sequence and transfected or transformed into a host cell. In the presence of TetR, which is co-transfected into the host cell, expression of the recombinant protein is repressed due to binding of the TetR protein to the tetO regulatory element. High-level, regulated gene expression can then be induced in response to varying concentrations of tetracycline (Tc) or Tc derivatives such as doxycycline (Dox), which compete with tetO elements for binding to TetR. Constructs and materials for tet inducible gene expression are available commercially from CLONTECH Laboratories, Inc., Palo Alto, Calif.

When used as a component in an assay system, the gene protein may be labeled, either directly or indirectly, to facilitate detection of a complex formed between the gene protein and a test substance. Any of a variety of suitable labeling systems may be used including but not limited to radioisotopes such as $^{125}I$; enzyme labeling systems that generate a detectable calorimetric signal or light when exposed to substrate; and fluorescent labels. Where recombinant DNA technology is used to produce the gene protein for such assay systems, it may be advantageous to engineer fusion proteins that can facilitate labeling, immobilization and/or detection.

Indirect labeling involves the use of a protein, such as a labeled antibody, which specifically binds to the gene product. Such antibodies include but are not limited to polyclonal, monoclonal, chimeric, single chain, Fab fragments and fragments produced by a Fab expression library.

Production of Antibodies

Described herein are methods for the production of antibodies capable of specifically recognizing one or more epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a glucagon receptor gene in a biological sample, or, alternatively, as a method for the inhibition of abnormal glucagon receptor gene activity. Thus, such antibodies may be utilized as part of disease treatment methods, and/or may be used as part of diagnostic techniques whereby patients may be tested for abnormal levels of glucagon receptor gene proteins, or for the presence of abnormal forms of such proteins.

For the production of antibodies, various host animals may be immunized by injection with the glucagon receptor gene, its expression product or a portion thereof. Such host animals may include but are not limited to rabbits, mice, rats, goats and chickens, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*bacille Calmette-Guerin*) and *Corynebacterium parvum*.

Polyclonal antibodies are heterogeneous populations of antibody molecules derived from the sera of animals immunized with an antigen, such as a glucagon receptor gene product, or an antigenic functional derivative thereof. For the production of polyclonal antibodies, host animals such as those described above, may be immunized by injection with gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to the hybridoma technique of Kohler and Milstein, *Nature,* 256:495–7 (1975); and U.S. Pat. No. 4,376,110), the human B-cell hybridoma technique (Kosbor, et al., *Immunology Today,* 4:72 (1983); Cote, et al., *Proc. Natl. Acad. Sci. USA,* 80:2026–30 (1983)), and the EBV-hybridoma technique (Cole, et al., in Monoclonal Antibodies And Cancer Therapy, Alan R. Liss, Inc., New York, pp. 77–96 (1985)). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., *Proc. Natl. Acad. Sci.,* 81:6851–6855 (1984); Takeda, et al., *Nature,* 314:452–54 (1985)) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, *Science* 242:423–26 (1988); Huston, et al., *Proc. Natl. Acad. Sci. USA,* 85:5879–83 (1988); and Ward, et al., *Nature,* 334:544–46 (1989)) can be adapted to produce gene-single chain antibodies. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries may be constructed (Huse, et al., *Science,* 246:1275–81 (1989)) to allow rapid and easy identification of monoclonal Fab fragments with the desired specificity.

Screening Methods

The present invention may be employed in a process for screening for agents such as agonists, i.e., agents that bind to and activate glucagon receptor polypeptides, or antagonists, i.e. inhibit the activity or interaction of glucagon receptor polypeptides with its ligand. Thus, polypeptides of the invention may also be used to assess the binding of small molecule substrates and ligands in, for example, cells, cell-free preparations, chemical libraries, and natural product mixtures as known in the art. Any methods routinely used to identify and screen for agents that can modulate receptors may be used in accordance with the present invention.

The present invention provides methods for identifying and screening for agents that modulate glucagon receptor expression or function. More particularly, cells that contain and express glucagon receptor gene sequences may be used to screen for therapeutic agents. Such cells may include non-recombinant monocyte cell lines, such as U937 (ATCC# CRL-1593), THP-1 (ATCC# TIB-202), and P388D1 (ATCC# TIB-63); endothelial cells such as HUVEC's and bovine aortic endothelial cells (BAEC's); as well as generic mammalian cell lines such as HeLa cells and COS cells, e.g., COS-7 (ATCC# CRL-1651). Further, such cells may include recombinant, transgenic cell lines. For example, the transgenic mice of the invention may be used to generate cell lines, containing one or more cell types involved in a disease, that can be used as cell culture models for that disorder. While cells, tissues, and primary cultures derived from the disease transgenic animals of the invention may be utilized, the generation of continuous cell lines is preferred. For examples of techniques that may be used to derive a continuous cell line from the transgenic animals, see Small, et al., *Mol. Cell Biol.,* 5:642–48 (1985).

Glucagon receptor gene sequences may be introduced into and overexpressed in the genome of the cell of interest. In order to overexpress a glucagon receptor gene sequence, the coding portion of the glucagon receptor gene sequence may be ligated to a regulatory sequence that is capable of driving gene expression in the cell type of interest. Such regulatory regions will be well known to those of skill in the art, and may be utilized in the absence of undue experimentation. Glucagon receptor gene sequences may also be disrupted or underexpressed. Cells having glucagon receptor gene disruptions or underexpressed glucagon receptor gene sequences may be used, for example, to screen for agents capable of affecting alternative pathways that compensate for any loss of function attributable to the disruption or underexpression.

In vitro systems may be designed to identify compounds capable of binding the glucagon receptor gene products. Such compounds may include, but are not limited to, peptides made of D-and/or L-configuration amino acids (in, for example, the form of random peptide libraries; (see e.g., Lam, et al., *Nature,* 354:82–4 (1991)), phosphopeptides (in, for example, the form of random or partially degenerate, directed phosphopeptide libraries; see, e.g., Songyang, et al., *Cell,* 72:767–78 (1993)), antibodies, and small organic or inorganic molecules. Compounds identified may be useful, for example, in modulating the activity of glucagon receptors, preferably mutant glucagon receptors; elaborating the biological function of the glucagon receptor gene protein; or screening for compounds that disrupt normal glucagon receptor gene interactions or themselves disrupt such interactions.

The principle of the assays used to identify compounds that bind to the glucagon receptor involves preparing a reaction mixture of the glucagon receptor and the test compound under conditions and for a time sufficient to allow the two components to interact and bind, thus forming a complex that can be removed and/or detected in the reaction mixture. These assays can be conducted in a variety of ways. For example, one method to conduct such an assay would involve anchoring the glucagon receptor or the test substance onto a solid phase and detecting target protein/test substance complexes anchored on the solid phase at the end of the reaction. In one embodiment of such a method, the glucagon receptor may be anchored onto a solid surface, and the test compound, which is not anchored, may be labeled, either directly or indirectly.

In practice, microtitre plates are conveniently utilized. The anchored component may be immobilized by non-covalent or covalent attachments. Non-covalent attachment may be accomplished simply by coating the solid surface with a solution of the protein and drying. Alternatively, an immobilized antibody, preferably a monoclonal antibody, specific for the protein may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for the glucagon receptor gene product or the test compound to anchor any complexes formed in solution, and a labeled antibody specific for the other component of the possible complex to detect anchored complexes.

Compounds that are shown to bind to a particular glucagon receptor gene product through one of the methods described above can be further tested for their ability to elicit a biochemical response from the glucagon receptor gene protein. Agonists, antagonists and/or inhibitors of the expression product can be identified utilizing assays well known in the art.

Antisense, Ribozymes, and Antibodies

Other agents that may be used as therapeutics include the glucagon receptor gene, its expression product(s) and functional fragments thereof. Additionally, agents that reduce or inhibit mutant glucagon receptor gene activity may be used to ameliorate disease symptoms. Such agents include antisense, ribozyme, and triple helix molecules. Techniques for the production and use of such molecules are well known to those of skill in the art.

Anti-sense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the glucagon receptor gene nucleotide sequence of interest, are preferred.

Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage. The composition of ribozyme molecules must include one or more sequences complementary to the glucagon receptor gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding glucagon receptor gene proteins.

Specific ribozyme cleavage sites within any potential RNA target are initially identified by scanning the molecule of interest for ribozyme cleavage sites that include the following sequences, GUA, GUU and GUC. Once identified, short RNA sequences of between 15 and 20 ribonucleotides corresponding to the region of the glucagon receptor gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription should be single stranded and composed of deoxyribonucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

It is possible that the antisense, ribozyme, and/or triple helix molecules described herein may reduce or inhibit the transcription (triple helix) and/or translation (antisense, ribozyme) of mRNA produced by both normal and mutant glucagon receptor gene alleles. In order to ensure that substantially normal levels of glucagon receptor gene activity are maintained, nucleic acid molecules that encode and express glucagon receptor polypeptides exhibiting normal activity may be introduced into cells that do not contain sequences susceptible to whatever antisense, ribozyme, or triple helix treatments are being utilized. Alternatively, it may be preferable to coadminister normal glucagon receptor protein into the cell or tissue in order to maintain the requisite level of cellular or tissue glucagon receptor gene activity.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Antibodies that are both specific for the glucagon receptor protein, and in particular, the mutant glucagon receptor protein, and interfere with its activity may be used to inhibit mutant glucagon receptor gene function. Such antibodies may be generated against the proteins themselves or against peptides corresponding to portions of the proteins using standard techniques known in the art and as also described herein. Such antibodies include but are not limited to polyclonal, monoclonal, Fab fragments, single chain antibodies, chimeric antibodies, antibody mimetics, etc.

In instances where the glucagon receptor protein is intracellular and whole antibodies are used, internalizing antibodies may be preferred. However, lipofectin liposomes may be used to deliver the antibody or a fragment of the Fab region that binds to the glucagon receptor gene epitope into cells. Where fragments of the antibody are used, the smallest inhibitory fragment that binds to the target or expanded target protein's binding domain is preferred. For example, peptides having an amino acid sequence corresponding to the domain of the variable region of the antibody that binds to the glucagon receptor protein may be used. Such peptides may be synthesized chemically or produced via recombinant DNA technology using methods well known in the art (see, e.g., Creighton, Proteins: Structures and Molecular Principles (1984) W. H. Freeman, New York 1983, supra; and Sambrook, et al., 1989, supra). Alternatively, single chain neutralizing antibodies that bind to intracellular glucagon receptor gene epitopes may also be administered. Such single chain antibodies may be administered, for example, by expressing nucleotide sequences encoding single-chain antibodies within the target cell population by utilizing, for example, techniques such as those described in Marasco, et al., *Proc. Natl. Acad. Sci. USA,* 90:7889–93 (1993).

RNA sequences encoding the glucagon receptor protein may be directly administered to a patient exhibiting disease symptoms, at a concentration sufficient to produce a level of glucagon receptor protein such that disease symptoms are ameliorated. Patients may be treated by gene replacement therapy. One or more copies of a normal glucagon receptor gene, or a portion of the gene that directs the production of a normal glucagon receptor protein with glucagon receptor gene function, may be inserted into cells using vectors that include, but are not limited to adenovirus, adeno-associated virus, and retrovirus vectors, in addition to other particles that introduce DNA into cells, such as liposomes. Additionally, techniques such as those described above may be utilized for the introduction of normal glucagon receptor gene sequences into human cells.

Cells, preferably autologous cells, containing normal glucagon receptor gene expressing gene sequences may then be introduced or reintroduced into the patient at positions that allow for the amelioration of disease symptoms.

Pharmaceutical Compositions, Effective Dosages, and Routes of Administration

The identified compounds that inhibit target mutant gene expression, synthesis and/or activity can be administered to a patient at therapeutically effective doses to treat or ameliorate the disease. A therapeutically effective dose refers to that amount of the compound sufficient to result in amelioration of symptoms of the disease.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral, topical, subcutaneous, intraperitoneal, intravenous, intrapleural, intraocular, intraarterial, or rectal administration. It is also contemplated that pharmaceutical compositions may be administered with other products that potentiate the activity of the compound and optionally, may include other therapeutic ingredients.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. Oral ingestion is possibly the easiest method of taking any medication. Such a route of administration, is generally simple and straightforward and is frequently the least inconvenient or unpleasant route of administration from the patient's point of view. However, this involves passing the material through the stomach, which is a hostile environment for many materials, including proteins and other biologically active compositions. As the acidic, hydrolytic and proteolytic environment of the stomach has evolved efficiently to digest proteinaceous materials into amino acids and oligopeptides for subsequent anabolism, it is hardly surprising that very little or any of a wide variety of biologically active proteinaceous material, if simply taken orally, would survive its passage through the stomach to be taken up by the body in the small intestine. The result, is that many proteinaceous medicaments must be taken in through another method, such as parenterally, often by subcutaneous, intramuscular or intravenous injection.

Pharmaceutical compositions may also include various buffers (e.g., Tris, acetate, phosphate), solubilizers (e.g., Tween, Polysorbate), carriers such as human serum albumin, preservatives (thimerosol, benzyl alcohol) and anti-oxidants such as ascorbic acid in order to stabilize pharmaceutical activity. The stabilizing agent may be a detergent, such as tween-20, tween-80, NP-40 or Triton X-100. EBP may also be incorporated into particulate preparations of polymeric compounds for controlled delivery to a patient over an extended period of time. A more extensive survey of components in pharmaceutical compositions is found in Remington's Pharmaceutical Sciences, 18th ed., A. R. Gennaro, ed., Mack Publishing, Easton, Pa. (1990).

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

Diagnostics

A variety of methods may be employed to diagnose disease conditions associated with the glucagon receptor gene. Specifically, reagents may be used, for example, for the detection of the presence of glucagon receptor gene mutations, or the detection of either over- or under-expression of glucagon receptor gene niRNA.

According to the diagnostic and prognostic method of the present invention, alteration of the wild-type glucagon receptor gene locus is detected. In addition, the method can be performed by detecting the wild-type glucagon receptor gene locus and confirming the lack of a predisposition or neoplasia. "Alteration of a wild-type gene" encompasses all forms of mutations including deletions, insertions and point mutations in the coding and noncoding regions. Deletions may be of the entire gene or only a portion of the gene. Point mutations may result in stop codons, frameshift mutations or amino acid substitutions. Somatic mutations are those that occur only in certain tissues, e.g., in tumor tissue, and are not inherited in the germline. Germline mutations can be found in any of a body's tissues and are inherited. If only a single allele is somatically mutated, an early neoplastic state may be indicated. However, if both alleles are mutated, then a late neoplastic state may be indicated. The finding of gene mutations thus provides both diagnostic and prognostic information. A glucagon receptor gene allele that is not deleted (e.g., that found on the sister chromosome to a chromosome carrying a glucagon receptor gene deletion) can be screened for other mutations, such as insertions, small deletions, and point mutations. Mutations found in tumor tissues may be linked to decreased expression of the glucagon receptor gene product. However, mutations leading to non-functional gene products may also be linked to a cancerous state. Point mutational events may occur in regulatory regions, such as in the promoter of the gene, leading to loss or diminution of expression of the mRNA. Point mutations may also abolish proper RNA processing, leading to loss of expression of the glucagon receptor gene product, or a decrease in mRNA stability or translation efficiency.

One test available for detecting mutations in a candidate locus is to directly compare genomic target sequences from cancer patients with those from a control population. Alternatively, one could sequence messenger RNA after amplification, e.g., by PCR, thereby eliminating the necessity of determining the exon structure of the candidate gene. Mutations from cancer patients falling outside the coding region of the glucagon receptor gene can be detected by examining the non-coding regions, such as introns and regulatory sequences near or within the glucagon receptor gene. An early indication that mutations in noncoding regions are important may come from Northern blot experiments that reveal messenger RNA molecules of abnormal size or abundance in cancer patients as compared to control individuals.

The methods described herein may be performed, for example, by utilizing pre-packaged diagnostic kits comprising at least one specific gene nucleic acid or anti-gene antibody reagent described herein, which may be conveniently used, e.g., in clinical settings, to diagnose patients exhibiting disease symptoms or at risk for developing disease.

Any cell type or tissue, including brain, cortex, subcortical region, cerebellum, brainstem, olfactory bulb, spinal cord, eye, Harderian gland, heart, lung, liver, pancreas, kidney, spleen, thymus, lymph nodes, bone marrow, skin, gallbladder, urinary bladder, pituitary gland, adrenal gland, salivary gland, skeletal muscle, tongue, stomach, small intestine, large intestine, cecum, testis, epididymis, seminal vesicle, coagulating gland, prostate gland, ovary, uterus and white fat, in which the gene is expressed may be utilized in the diagnostics described below.

DNA or RNA from the cell type or tissue to be analyzed may easily be isolated using procedures that are well known to those in the art. Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, PCR In Situ Hybridization: Protocols and Applications, Raven Press, N.Y. (1992)).

Gene nucleotide sequences, either RNA or DNA, may, for example, be used in hybridization or amplification assays of biological samples to detect disease-related gene structures and expression. Such assays may include, but are not limited to, Southern or Northern analyses, restriction fragment length polymorphism assays, single stranded conformational polymorphism analyses, in situ hybridization assays, and polymerase chain reaction analyses. Such analyses may reveal both quantitative aspects of the expression pattern of the gene, and qualitative aspects of the gene expression and/or gene composition. That is, such aspects may include, for example, point mutations, insertions, deletions, chromosomal rearrangements, and/or activation or inactivation of gene expression.

Preferred diagnostic methods for the detection of gene-specific nucleic acid molecules may involve for example, contacting and incubating nucleic acids, derived from the cell type or tissue being analyzed, with one or more labeled nucleic acid reagents under conditions favorable for the specific annealing of these reagents to their complementary sequences within the nucleic acid molecule of interest. Preferably, the lengths of these nucleic acid reagents are at least 9 to 30 nucleotides. After incubation, all non-annealed nucleic acids are removed from the nucleic acid:fingerprint molecule hybrid. The presence of nucleic acids from the fingerprint tissue that have hybridized, if any such molecules exist, is then detected. Using such a detection scheme, the nucleic acid from the tissue or cell type of interest may be immobilized, for example, to a solid support such as a membrane, or a plastic surface such as that on a microtitre plate or polystyrene beads. In this case, after incubation, non-annealed, labeled nucleic acid reagents are easily removed. Detection of the remaining, annealed, labeled nucleic acid reagents is accomplished using standard techniques well-known to those in the art.

Alternative diagnostic methods for the detection of gene-specific nucleic acid molecules may involve their amplification, e.g., by PCR (the experimental embodiment set forth in Mullis U.S. Pat. No. 4,683,202 (1987)), ligase chain reaction (Barany, Proc. Natl. Acad. Sci. USA, 88:189–93 (1991)), self sustained sequence replication (Guatelli, et al., Proc. Natl. Acad. Sci. USA, 87:1874–78 (1990)), transcriptional amplification system (Kwoh, et al., Proc. Natl. Acad. Sci. USA, 86:1173–77 (1989)), Q-Beta Replicase (Lizardi et al., Bio/Technology, 6:1197 (1988)), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA may be isolated include any tissue in which wild-type fingerprint gene is known to be expressed, including, but not limited to, brain, cortex, subcortical region, cerebellum, brainstem, olfactory bulb, spinal cord, eye, Harderian gland, heart, lung, liver, pancreas, kidney, spleen, thymus, lymph nodes, bone marrow, skin, gallbladder, urinary bladder, pituitary gland, adrenal gland, salivary gland, skeletal muscle, tongue, stomach, small intestine, large intestine, cecum, testis, epididymis, seminal vesicle, coagulating gland, prostate gland, ovary, uterus and white fat. A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method may be chosen from among the gene nucleic acid reagents described herein. The preferred lengths of such nucleic acid reagents are at least 15–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Antibodies directed against wild-type or mutant gene peptides may also be used as disease diagnostics and prognostics. Such diagnostic methods, may be used to detect abnormalities in the level of gene protein expression, or abnormalities in the structure and/or tissue, cellular, or subcellular location of fingerprint gene protein. Structural differences may include, for example, differences in the size, electronegativity, or antigenicity of the mutant fingerprint gene protein relative to the normal fingerprint gene protein.

Protein from the tissue or cell type to be analyzed may easily be detected or isolated using techniques that are well known to those of skill in the art, including but not limited to western blot analysis. For a detailed explanation of methods for carrying out western blot analysis, see Sambrook, et al. (1989) supra, at Chapter 18. The protein detection and isolation methods employed herein may also be such as those described in Harlow and Lane, for example, (Antibodies: A Laboratory Manual, Cold Spring Harbor Laboratory Press, Cold Spring Harbor, N.Y. (1988)).

Preferred diagnostic methods for the detection of wild-type or mutant gene peptide molecules may involve, for example, immunoassays wherein fingerprint gene peptides are detected by their interaction with an anti-fingerprint gene-specific peptide antibody.

For example, antibodies, or fragments of antibodies useful in the present invention may be used to quantitatively or qualitatively detect the presence of wild-type or mutant gene peptides. This can be accomplished, for example, by immunofluorescence techniques employing a fluorescently labeled antibody (see below) coupled with light microscopic, flow cytometric, or fluorimetric detection. Such techniques are especially preferred if the fingerprint gene peptides are expressed on the cell surface.

The antibodies (or fragments thereof) useful in the present invention may, additionally, be employed histologically, as in immunofluorescence or immunoelectron microscopy, for in situ detection of fingerprint gene peptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified in order to achieve such in situ detection.

Immunoassays for wild-type, mutant, or expanded fingerprint gene peptides typically comprise incubating a biological sample, such as a biological fluid, a tissue extract, freshly harvested cells, or cells that have been incubated in tissue culture, in the presence of a detectably labeled antibody capable of identifying fingerprint gene peptides, and detecting the bound antibody by any of a number of techniques well known in the art.

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled gene-specific antibody. The solid phase support may then be washed with the buffer a second time to remove unbound antibody. The amount of bound label on solid support may then be detected by conventional means.

The terms "solid phase support or carrier" are intended to encompass any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild-type or -mutant fingerprint gene peptide antibody may be determined according to well known methods. Those skilled in the art will be able to determine operative and optimal assay conditions for each determination by employing routine experimentation.

One of the ways in which the gene peptide-specific antibody can be detectably labeled is by linking the same to an enzyme and using it in an enzyme immunoassay (EIA) (Voller, *Ric Clin Lab,* 8:289–98 (1978) ["The Enzyme Linked Immunosorbent Assay (ELISA)", Diagnostic Horizons 2:1–7, 1978, Microbiological Associates Quarterly Publication, Walkersville, Md.]; Voller, et al., *J. Clin. Pathol.,* 31:507–20 (1978); Butler, *Meth. Enzymol.,* 73:482–523 (1981); Maggio (ed.), Enzyme Immunoassay, CRC Press, Boca Raton, Fla. (1980); Ishikawa, et al., (eds.) Enzyme Immunoassay, Igaku-Shoin, Tokyo (1981)). The enzyme that is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild-type, mutant, or expanded peptides through the use of a radioimmunoassay (RIA) (see, e.g., Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Throughout this application, various publications, patents and published patent applications are referred to by an identifying citation. The disclosures of these publications, patents and published patent specifications referenced in this application are hereby incorporated by reference into the present disclosure to more fully describe the state of the art to which this invention pertains.

The following examples are intended only to illustrate the present invention and should in no way be construed as limiting the subject invention.

EXAMPLES

Example 1

Generation of Mice Comprising Glucagon Receptor Gene Disruptions

To investigate the role of glucagon receptors, disruptions in glucagon receptor genes were produced by homologous recombination. Specifically, transgenic mice comprising disruptions in glucagon receptor genes were created. More particularly, as shown in FIG. 2, a glucagon receptor targeting construct having the ability to disrupt a glucagon receptor gene was created, using as the targeting in the construct the oligonucleotide sequences identified herein as SEQ ID NO:3 or SEQ ID NO:4.

The targeting construct was introduced into ES cells derived from the 129/OlaHsd mouse substrain to generate chimeric mice. The F1 mice were generated by breeding with C57Bu6 females, and the resultant F1NO heterozygotes were backcrossed to C57BL/6 mice to generate F1N1 heterozygotes. The F2N1 homozygous mutant mice were produced by intercrossing F1N1 heterozygous males and females.

The transgenic mice comprising disruptions in glucagon receptor genes were analyzed for phenotypic changes and expression patterns. The phenotypes associated with a disruption in the glucagon receptor gene were determined.

Example 2

Expression Analysis

RT-PCR Expression. Total RNA was isolated from the organs or tissues from adult C57BL/6 wild-type mice. RNA was DNaseI treated, and reverse transcribed using random primers. The resulting cDNA was checked for the absence of genomic contamination using primers specific to non-transcribed genomic mouse DNA. cDNAs were balanced for concentration using HPRT primers. RNA transcripts were detectable in liver, kidney, gall bladder, adrenal gland and salivary gland. RNA transcripts were not detectable in brain, cortex, subcortical region, cerebellum, brainstem, olfactory bulb, eye, heart, lung, pancreas, spleen, thymus, lymph nodes, bone marrow, skin, urinary bladder, pituitary gland, skeletal muscle, tongue, stomach, small intestine, large intestine, cecum, testis, epididymis, seminal vesicle, coagulating gland, prostate gland, ovary and uterus.

Example 3

Analysis of Transgenic Mice

Histopathology: When compared to age- and gender-matched wild-type control mice, the transgenic mice comprising disruptions in the glucagon receptor displayed changes in the Islets of Langerhans cells of the pancreas at about 49 days of age. Specifically, all homozygous mutant female mice, three out of four homozygous mutant male mice, and one heterozygous mutant male mouse displayed mild to moderate hyperplasia and hypertrophy of the Islet cells, as well as increased cytoplasmic vacuolization and granularity. In addition, it was observed that one homozygous mutant male mouse displayed thymic atrophy and marked testicular immaturity, and this mouse was clinically identified as a dwarf.

Normal Islets of Langerhans cells are predominantly composed of insulin-secreting β-cells, with a narrow rim of glucagon-secreting α-cells, and a scattering of somatostatin-secreting δ-cells. Immunohistochemistry performed on tissues from homozygous animals demonstrated that α-cells were increased in number and size, while β-cells were reduced in number.

At about 300 days of age, all homozygous mutant mice displayed multiple pancreatic islet cell adenomas. All homozygous mutant mice and one wild-type control (male) mouse displayed islet cell hyperplasia. Increased cytoplasmic vacuolization and granularity was observed in both the islet cell adenomas and hyperplastic islet cells of the homozygous mutant mice relative to wild-type mice.

Necropsy—Body and Organ Weights: At about 49 days of age, the transgenic mice comprising disruptions in glucagon receptor genes generally displayed reduced body weights. In particular, some homozygous mutant (−/−) mice displayed reduced body weights relative to wild-type (+/+) control mice. In addition, some homozygous mutant mice displayed reduced organ weights. The supporting data is provided in the following Table 1.

TABLE 1

Body and Organ Weights

| Gender | Age at Test | Length (cm) | Body Weight (g) | Spleen Weight (g) | Liver Weight (g) | Kidney Weight (g) | Thymus Weight (g) | Heart Weight (g) | Testes + Epididy Weight (g) |
|---|---|---|---|---|---|---|---|---|---|
| +/+ | | | | | | | | | |
| Female | 48 | 9.5 | 22.74 | 0.115 | 1.154 | 0.273 | 0.084 | 0.127 | |
| Female | 48 | 9.2 | 21.424 | 0.083 | 1.155 | 0.268 | 0.078 | 0.109 | |
| Male | 48 | 9.5 | 27.705 | 0.088 | 1.451 | 0.408 | 0.081 | 0.147 | 0.259 |
| Male | 49 | 9 | 27.979 | 0.096 | 1.542 | 0.415 | 0.079 | 0.162 | 0.312 |
| −/+ | | | | | | | | | |
| Female | 48 | 9.5 | 22.29 | 0.086 | 1.139 | 0.291 | 0.11 | 0.109 | |
| Female | 47 | 8.25 | 16.377 | 0.073 | 1.042 | 0.22 | 0.078 | 0.087 | |
| Female | 47 | 8.5 | 18.128 | 0.071 | 0.991 | 0.215 | 0.104 | 0.096 | |

TABLE 1-continued

Body and Organ Weights

| Gender | Age at Test | Length (cm) | Body Weight (g) | Spleen Weight (g) | Liver Weight (g) | Kidney Weight (g) | Thymus Weight (g) | Heart Weight (g) | Testes + Epididy Weight (g) |
|---|---|---|---|---|---|---|---|---|---|
| Female | 47 | 8 | 18.838 | 0.072 | 1.086 | 0.254 | 0.09 | 0.101 | |
| Male | 49 | 9.25 | 28.522 | 0.085 | 1.713 | 0.409 | 0.079 | 0.154 | 0.252 |
| Male | 49 | 9 | 23.867 | 0.098 | 1.488 | 0.332 | 0.059 | 0.141 | 0.239 |
| Male | 49 | 9.75 | 26.348 | 0.12 | 1.698 | 0.357 | 0.087 | 0.162 | 0.216 |
| Male | 48 | 9.5 | 27.488 | 0.101 | 1.596 | 0.381 | 0.094 | 0.194 | 0.285 |
| −/− | | | | | | | | | |
| Female | 48 | 7.25 | 9.715 | 0.019 | 0.344 | 0.225 | 0.01 | 0.057 | |
| Female | 48 | 8.5 | 20.1 | 0.076 | 1.204 | 0.285 | 0.068 | 0.112 | |
| Female | 48 | 9.5 | 22.034 | 0.086 | 1.406 | 0.343 | 0.08 | 0.124 | |
| Male | 48 | 9.4 | 22.127 | 0.066 | 1.174 | 0.314 | 0.061 | 0.121 | 0.258 |
| Male | 48 | 8.5 | 18.598 | 0.066 | 0.91 | 0.368 | 0.058 | 0.116 | 0.169 |
| Male | 54 | 9.5 | 24.785 | 0.086 | 1.563 | 0.443 | 0.073 | 0.135 | 0.283 |
| Male | 48 | 7.5 | 8.556 | 0.03 | 0.285 | 0.154 | 0.012 | 0.059 | 0.031 |
| Male | 45 | 5.25 | 5.279 | 0.009 | 0.177 | 0.098 | 0.007 | 0.048 | 0.037 |

Physical Exam: At about 49 days of age, the transgenic mice comprising disruptions in glucagon receptor genes exhibited abnormal body shape. Specifically, several homozygous mutant mice were identified as dwarf shaped.

Serum Chemistry: Serum samples from homozygous mutant mice, heterozygous mutant mice, and wild-type control mice were evaluated by a clinical chemistry panel. At about 49 days of age, transgenic mice comprising disruptions in glucagon receptors exhibited reduced serum glucose levels relative to wild-type (+/+) mice. Specifically, all homozygous (−/−) mutant female mice, two of three homozygous (−/−) mutant male mice, and one heterozygous (−/+) mutant male mouse displayed reduced serum glucose levels, as shown in Table 2 below. All animals exhibiting reduced serum glucose levels also displayed significant phenotypic histologic alterations of pancreatic islet cells, as noted above.

TABLE 2

Glucose levels

| Genotype | Gender | Age at Test (days) | Glucose (mg/dl) |
|---|---|---|---|
| +/+ | Female | 48 | 253 |
| | | 48 | 258 |
| +/+ | Male | 48 | 263 |
| | | 49 | 278 |
| −/+ | Female | 48 | 245 |
| | | 47 | 202 |
| | | 47 | 169 |
| −/+ | Male | 49 | 190 |
| | | 49 | 198 |
| | | 49 | 228 |
| | | 48 | 214 |
| −/− | Female | 48 | 148 |
| | | 62 | 151 |
| | | 49 | 131 |
| −/− | Male | 48 | 278 |
| | | 49 | 159 |
| | | 49 | 154 |

Figure 4:
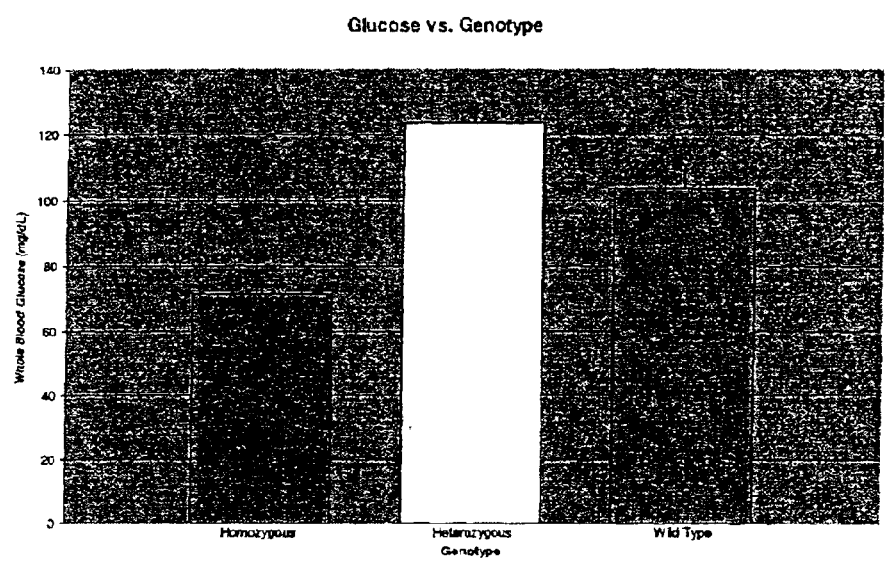
FIG. 4 shows the fasting whole blood glucose levels in homozygous, heterozygous, and wild-type mice.
Figure 5:
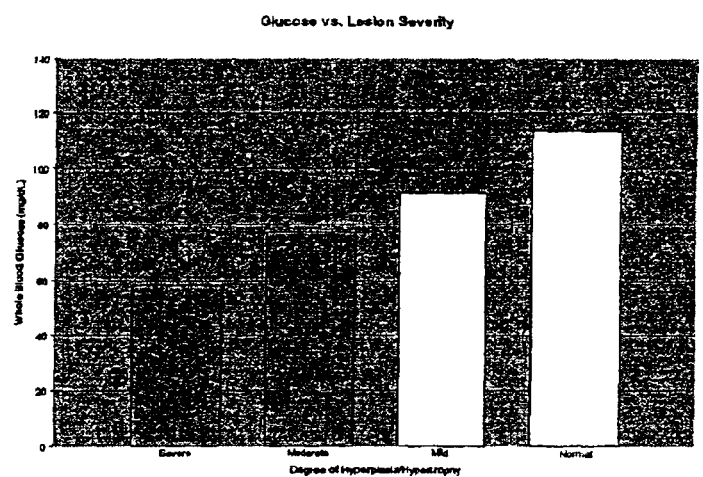
FIG. 5 shows data relating to the relationship of blood glucose levels to the severity of pancreatic lesions.
Figure 6:
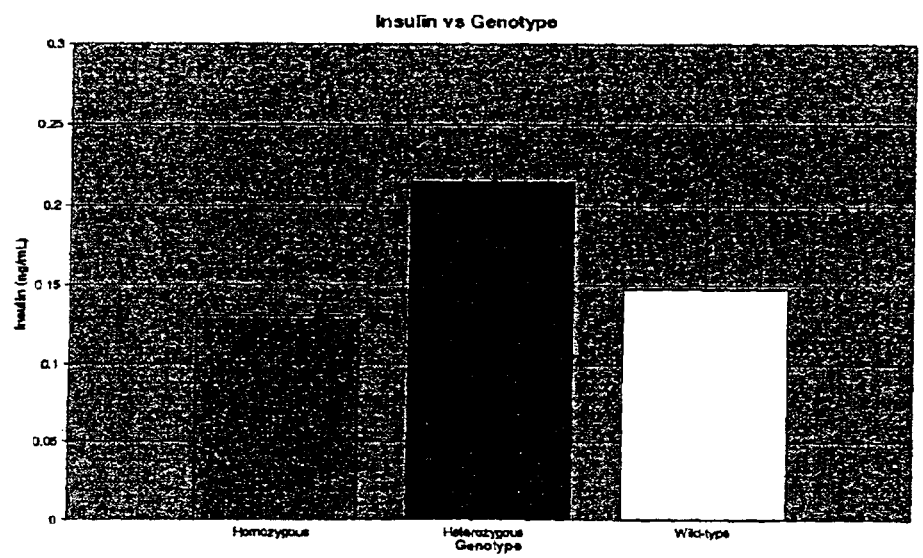
FIG. 6 shows data relating to serum insulin levels in homozygous, heterozygous, and wild-type mice.
Figure 7:
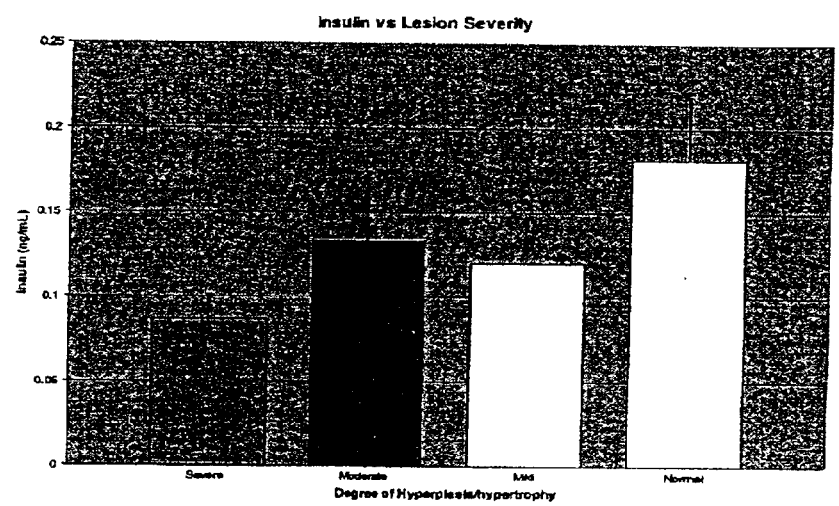
FIG. 7 shows data relating to the relationship of serum insulin levels to the severity of pancreatic lesions.
Figure 8:
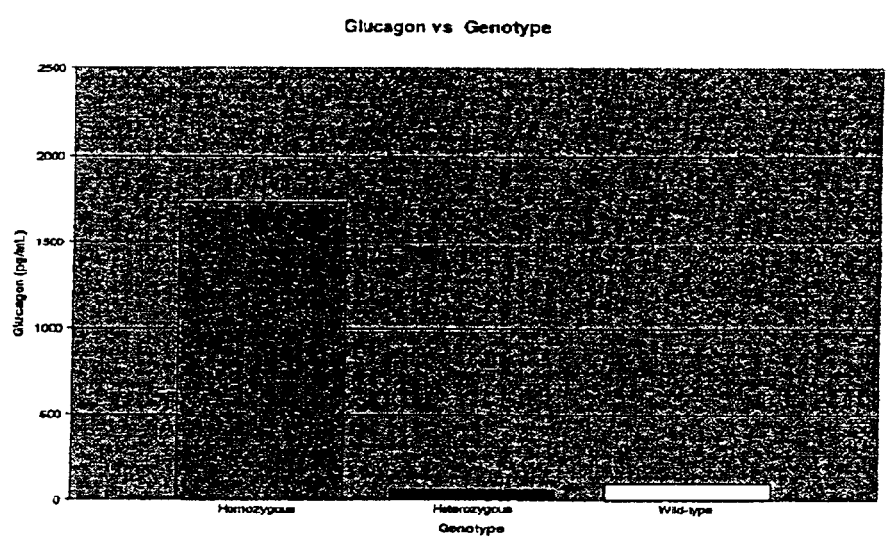
FIG. 8 shows the serum glucagon levels in homozygous, heterozygous, and wild-type mice.

At about 73 days of age, homozygous, heterozygous, and wild-type mice were analyzed for fasting whole blood glucose, serum insulin, and serum glucagon measurements. As shown in FIG. 4, fasting blood glucose was greatly decreased in homozygous mutant mice, while heterozygous mutant mice had increased fasting blood glucose levels. The relationship between blood glucose levels and the severity of pancreatic lesions is demonstrated in FIG. 5. Serum insulin levels were decreased in homozygous mutant mice, as shown in FIG. 6, and the relationship of insulin levels to the severity of pancreatic lesions is shown in FIG. 7. Glucagon levels were greatly elevated in homozygous mutant mice (see FIG. 8) and these levels also correlated with the severity of the pancreatic lesions.

Densitometry: A PIXImus densitometer, which utilizes Dual Energy X-ray absorptiometry (DXA), was used to measure fat as a percent of body soft tissue in approximately 73 day old mice. Homozygous mutant female and male mice (−/−) displayed decreased fat as a percent of body soft tissue when compared to age- and gender-matched wild-type control mice (+/+), as shown in Table 3 below.

TABLE 3

Fat as a Percent of Body Soft Tissue

| Genotype | Gender Mouse | Age at Test (days) | fat (% of body weight) |
|---|---|---|---|
| +/+ | Female | | |
| | 120215 | 73 | 14.71 |
| | 120229 | 73 | 15.71 |
| +/+ | Male | | |
| | 120212 | 73 | 12.1 |
| | 120213 | 73 | 13.65 |
| −/+ | Male | | |
| | 120210 | 73 | 13.03 |
| | 120219 | 73 | 13.02 |
| | 120221 | 73 | 14.76 |
| | 120223 | 73 | 17.56 |
| −/− | Female | | |
| | 120216 | 73 | 12.24 |
| | 120225 | 73 | 13.2 |
| | 120227 | 73 | 13.06 |
| | 120228 | 73 | 11.97 |
| −/− | Male | | |
| | 120211 | 73 | 11.32 |
| | 120220 | 73 | 9.99 |
| | 120222 | 73 | 11.64 |

Fertility: Three homozygous mutant mice of each gender were set up for mating one on one at about seven to eight weeks of age. The transgenic mice of the present invention were infertile. Specifically, two homozygous mutant females set up for mating were not able to have pups, and the remaining female was able to produce only one pup.

Example 4

Role of the Glucagon Receptor in Glucose Tolerance and Diabetes

To reveal the potential contribution of the glucagon receptor gene to type II diabetes and obesity, a series of tests were performed on glucagon deficient mice and wild-type control mice. These procedures included the Glucose Tolerance Test (GTT), the Insulin Suppression Test (IST) and the Glucose-stimulated Insulin Secretion Test (GSIST). Glucose tolerance, as seen in type II diabetes, can be the result of either insulin insensitivity, which is the inability of muscle, fat or liver cells to take up glucose in response to insulin, or insulin deficiency, usually the result of pancreatic β-cell dysfunction, or both. These tests are meant to measure the ability of the mice to metabolize and/or store glucose, the sensitivity of blood glucose to exogenous insulin, and insulin secretion in response to glucose.

Materials and Methods: Five homozygous mutant, six heterozygous mutant, and five wild-type male mice, approximately one year old were tested for glucose tolerance, insulin sensitivity, and glucose-stimulated insulin secretion. Mice were maintained on a 12 hour/12 hour dark/light cycle and were fed mouse chow diet (Harlan Teklad, Madison, Wis.) and water ad libitum. One week prior to the tests, mice were individually housed. On the day of testing, mice were fasted for 5 hours prior to measuring the basal glucose plasma concentration or insulin concentration. Water was still provided at will during this fasting period.

Glucose Tolerance Test (GTT): Tail vein blood glucose levels were measured before injection by collecting 5 to 10 microliters of blood from the tail tip and using glucometers (Glucometer Elite, BayerCorporation, Mishawaka, Ind.). The glucose values were used for time t=0. Mice were weighed at t=0 and glucose was then administered by i.p. injection at a dose of 2 grams per kilogram of body weight. Plasma glucose concentrations were measured at 15, 30, 60, 90, and 120 minutes after injection by the method used to measure basal (t=0) blood glucose.

Mice were returned to cages with access to food ad libitum for one week, after which the GTT was repeated. Glucose values of both tests were averaged for statistical analysis. Pair-wise statistical significance was established using a Student t-test. Weights and plasma glucose concentrations are presented as Mean±SE. Statistical significance is defined as P<0.05. The glucose levels presented were thought to be representative of the ability of the mouse to secrete insulin in response to elevated glucose levels and the ability of muscle, liver and adipose tissues to uptake glucose.

Insulin Suppression Test (IST): Tail vein glucose levels and body weight were measured at t=0 as in the GTT above. Insulin (Humulin R, Eli Lilly and Company, Indianapolis, Ind.) was administered by i.p injection at 0.5 Units per kilogram body weight. Plasma glucose levels were measured at 15, 30, 60, 90, and 120 minutes after insulin injection and presented as the percent of basal glucose. Glucose levels in this test were thought to be representative of the sensitivity of the mouse to insulin (ability of mouse tissues to uptake glucose in response to insulin).

Glucose-Stimulated Insulin Secretion Test (GSIST): Tail vein blood samples were taken before the test to measure serum insulin levels at t=0. Glucose was administerd by i.p injection at 2 grams per kilogram mouse body weight. Tail vein blood samples were then collected at 7.5, 15, 30, and 60 minutes after the glucose loading. Serum insulin levels were determined by an ELISA kit (Crystan Chem Inc., Chicago, Ill.).

After all three tests were completed, mice were then submitted to a high-fat (42%) diet (Adjusted Calories Diet #88137, Harlan Teklad, Madison, Wis.) for eight weeks. Mouse body weight and food intake are measured once weekly. GTT was repeated after the high-fat diet challenge.

Figure 9:
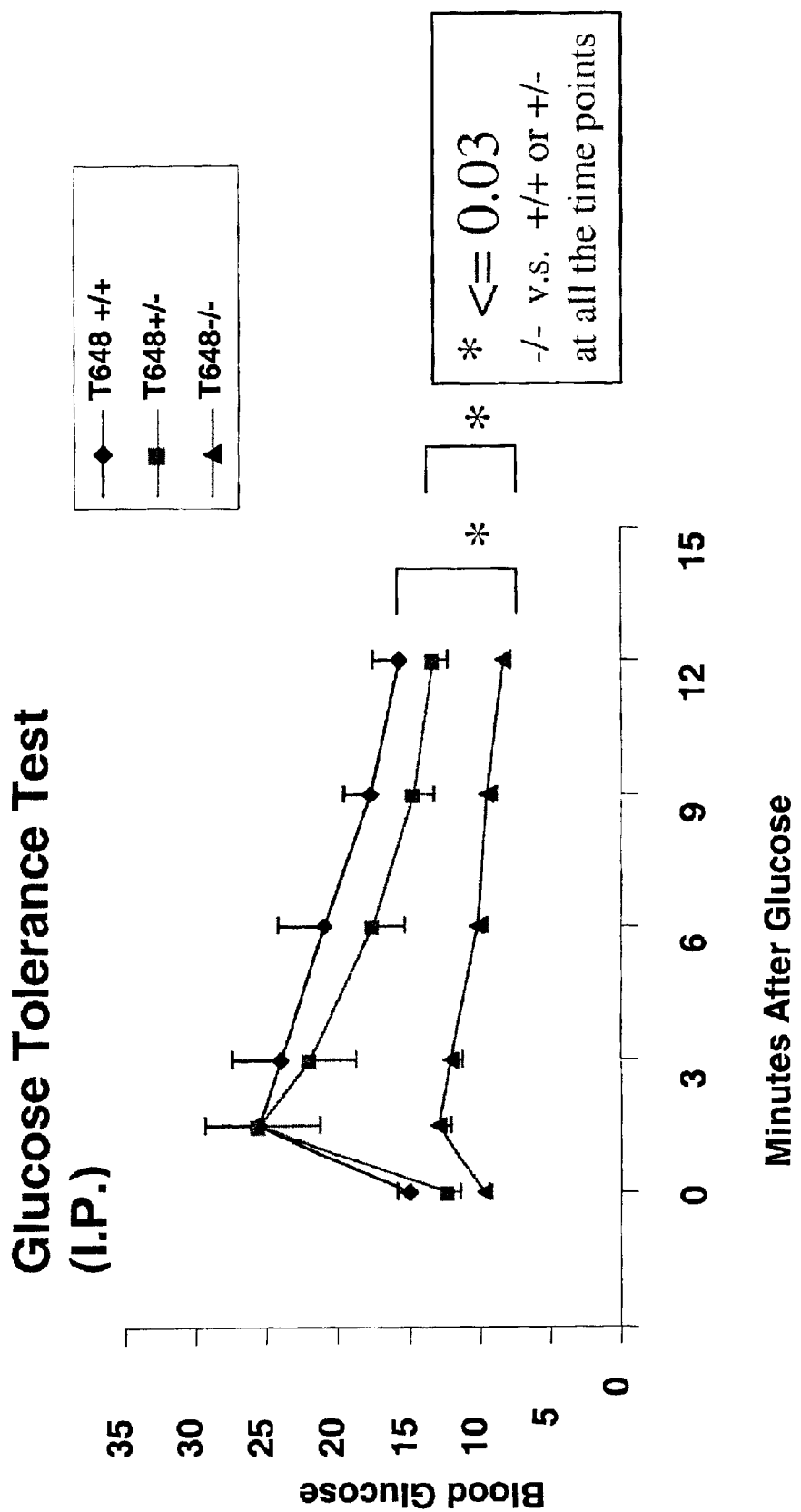
FIG. 9 shows the response of homozygous mutant mice, heterozygous mutant mice, and wild-type mice to a glucose challenge (Glucose tolerance test, GTT—before a high-fat diet challenge).

Results: The responses of control (+/+) and glucagon receptor mutant (−/− and −/+) mice to the GTT are shown in FIG. 9. Significant differences in plasma glucose concentrations were observed in homozygous mutant mice when compared to heterozygous mutant and wild-type mice at all time points after glucose injection ($p \leq 0.03$ for all time-points). It is also noted that fasting glucose levels are decreased in the homozygous mutant mice and heterozygous mutant mice when compared to wild-type mice. These results are indicative that glucagon receptor deficient mice were more tolerant to a glucose challenge relative to wild-type and heterozygous mutant mice, and that homozygous and heterozygous mutant mice have lower fasting glucose levels.

Figure 10:
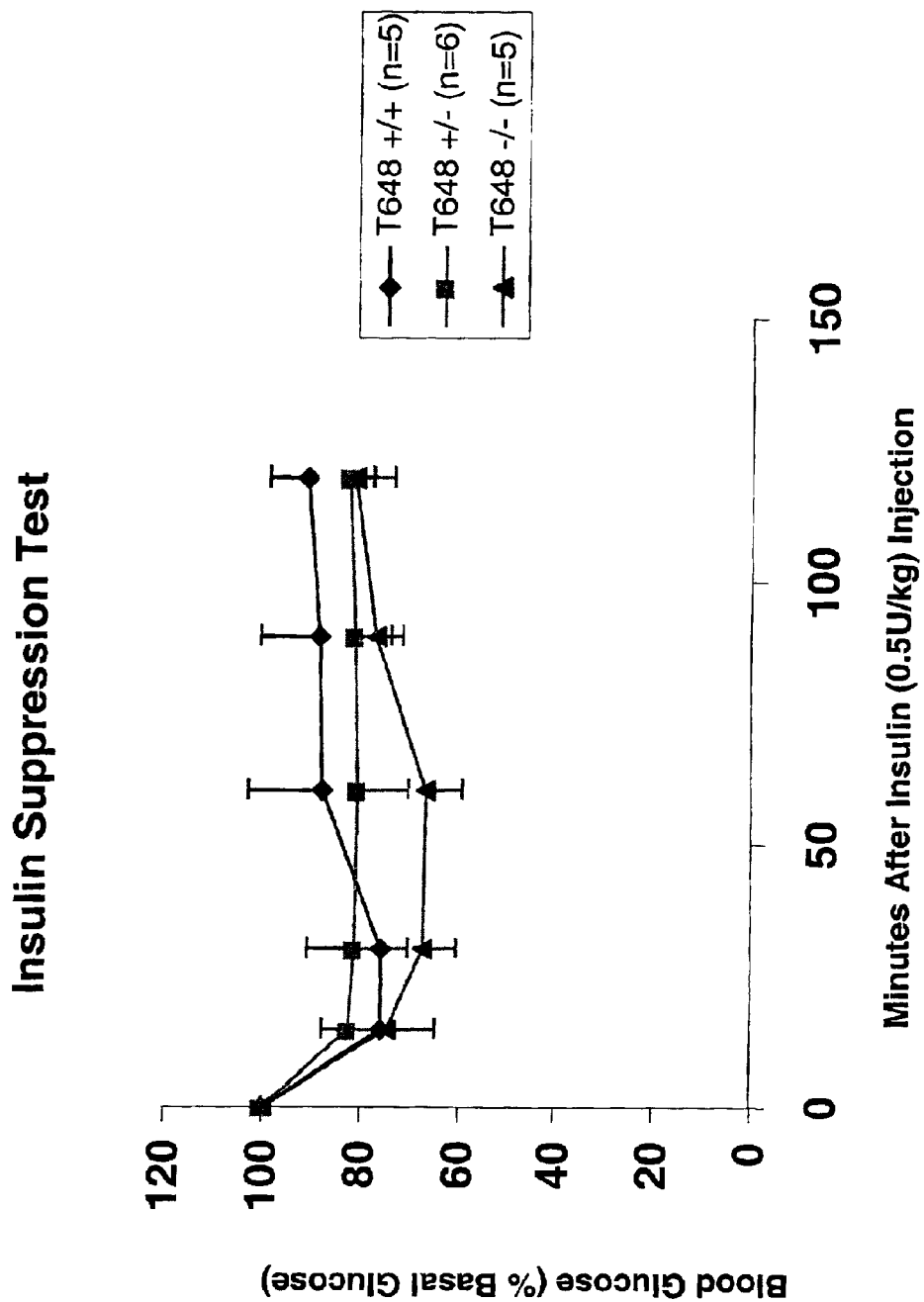
FIG. 10 shows the response of homozygous, heterozygous, and wild-type mice to insulin in the insulin suppression test (IST).
Figure 11:
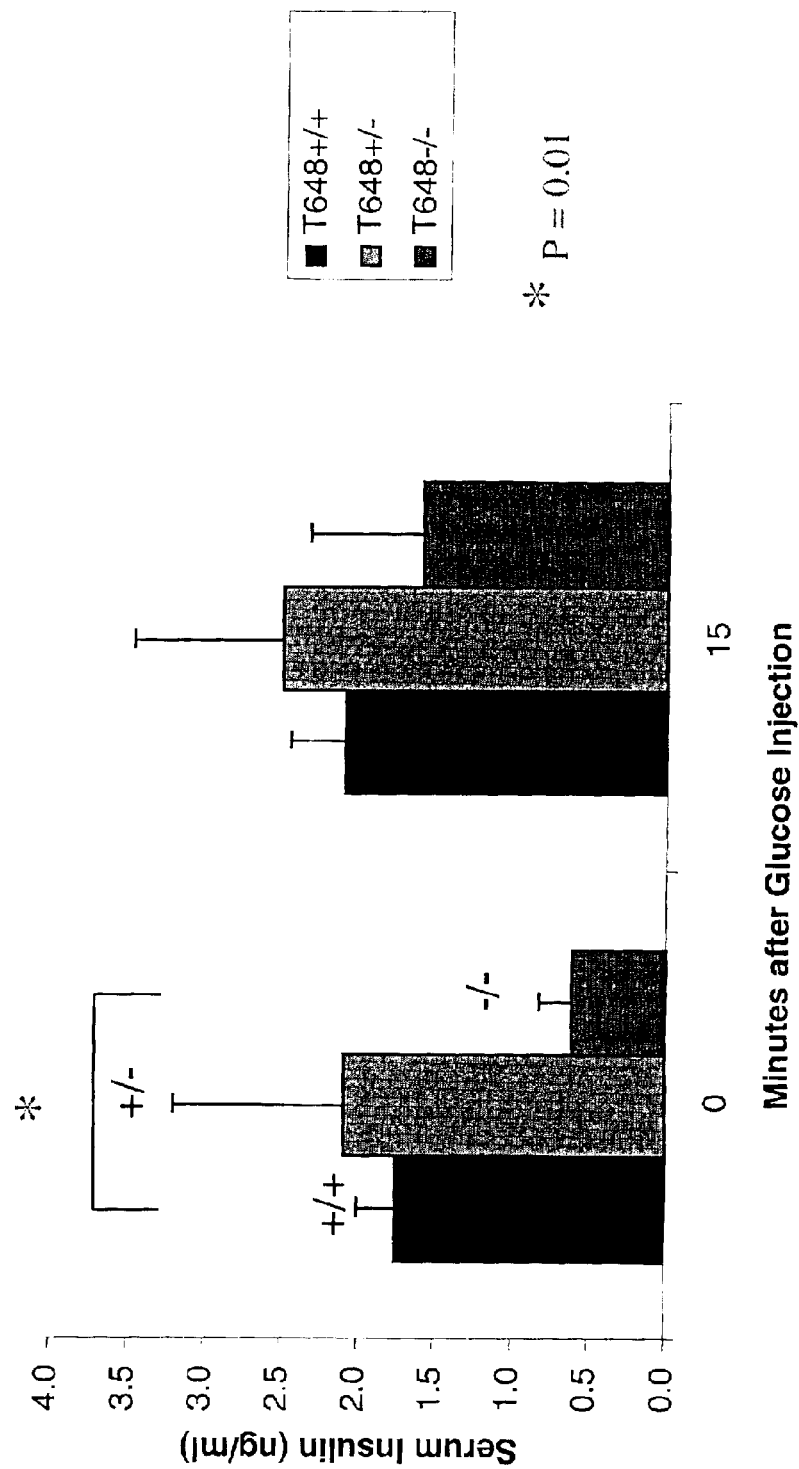
FIG. 11 shows the insulin response of homozygous, heterozygous, and wild-type mice to a glucose load (Glucose-stimulated insulin secretion test, GSIST).

As shown in FIG. 10, no difference in glucose levels was seen between homozygous mutant (−/−), heterozygous mutant (−/+), and wild-type mice (+/+) after injection with insulin, indicating that there is not a significant difference in the sensitivity of blood glucose in these glucagon receptor deficient mice to exogenous insulin. This suggests that it is possible that increased insulin sensitivity is not the mechanism for the increased glucose tolerance in the homozygous mutant mice. The results of the GSIST, shown in FIG. 11, show that the homozygous mutant mice (−/−) have lower fasting insulin levels when compared to wild-type mice (+/+), with no difference detected at 15 minutes post glucose injection, indicating the possibility that increased insulin levels are also not the mechanism for the increased glucose tolerance in glucagon receptor deficient mice.

Figure 12:
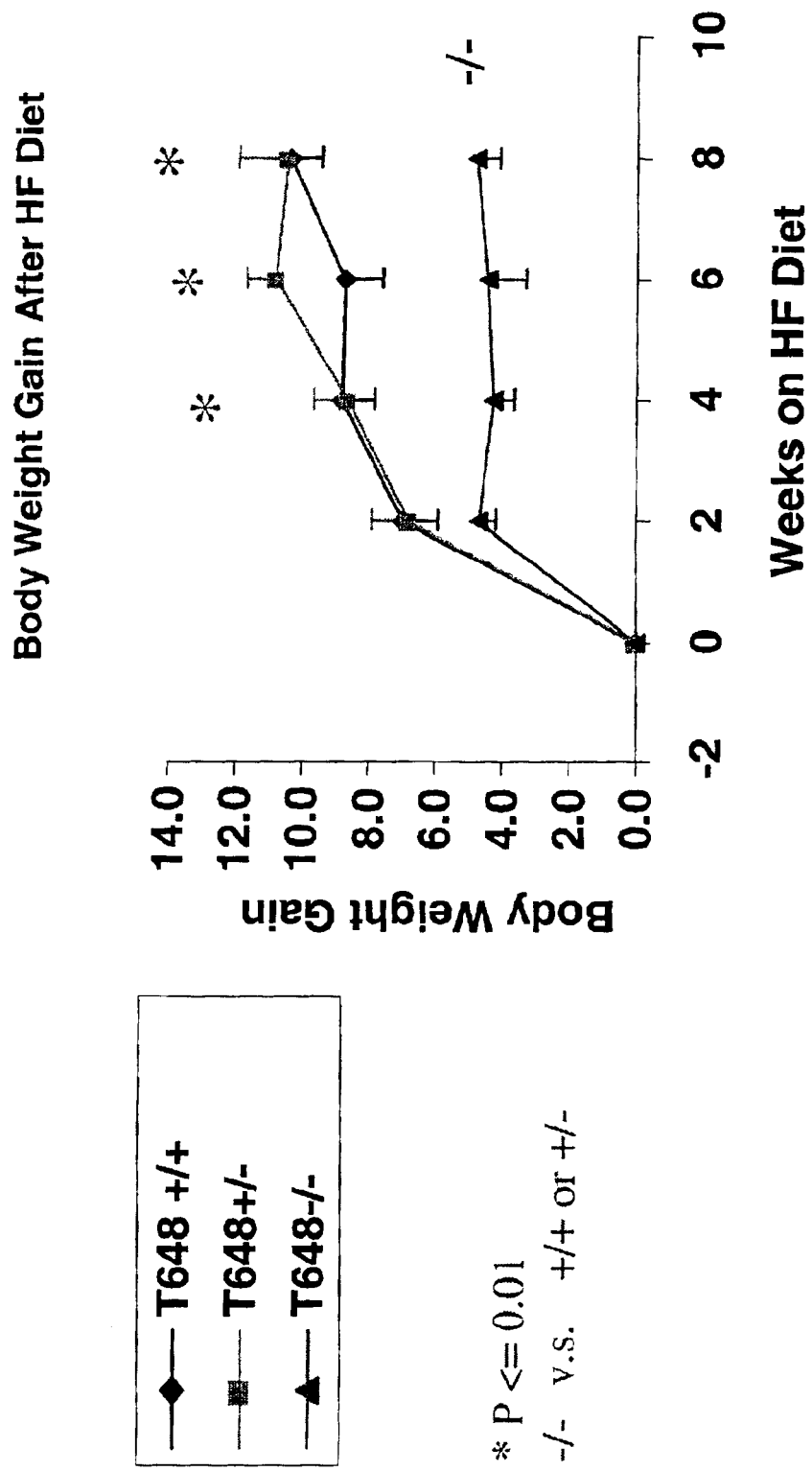
FIG. 12 shows the body weight gain of homozygous mutant, heterozygous mutant, and wild-type mice after eight weeks on a high-fat diet.
Figure 13:
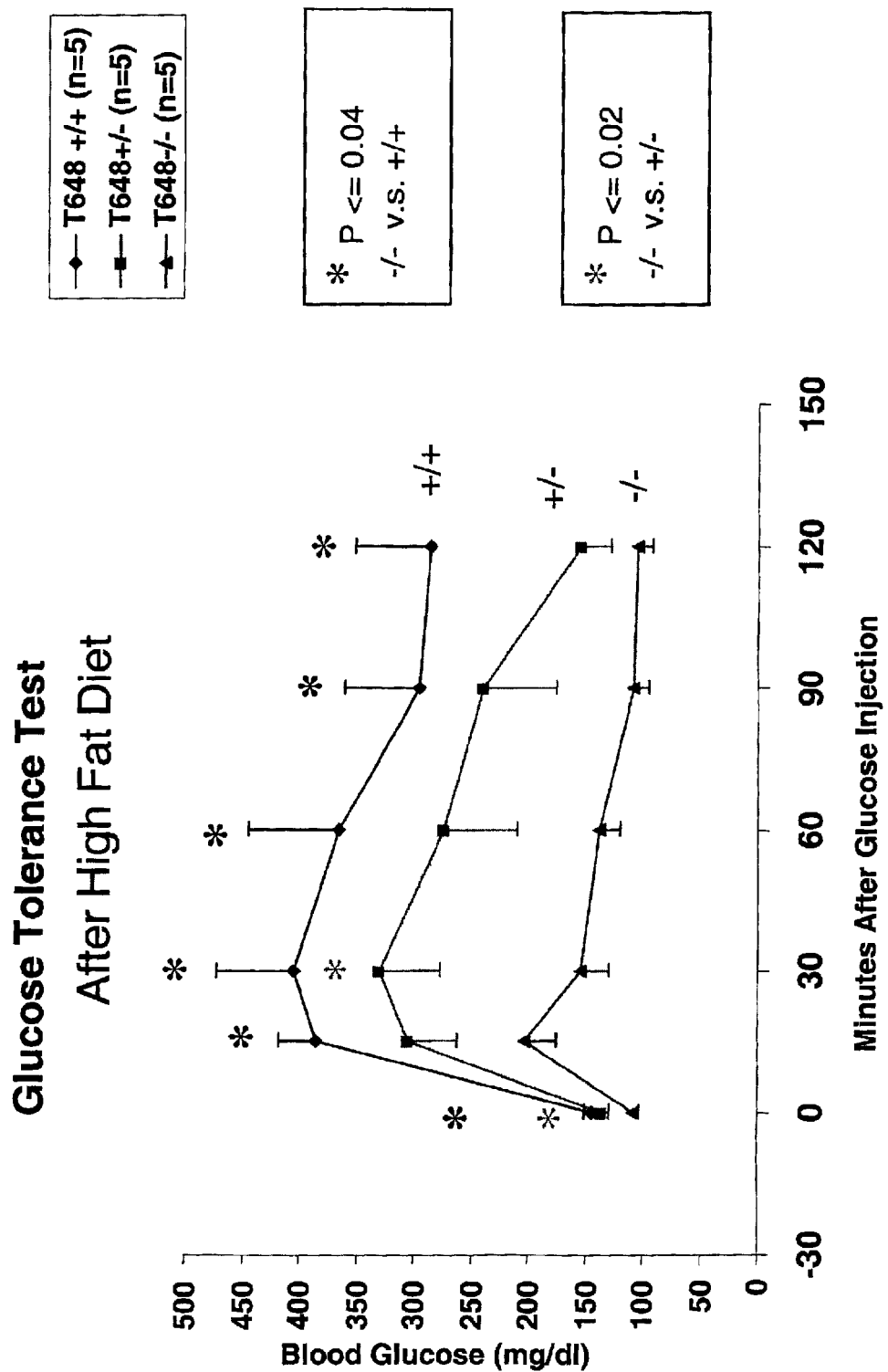
FIG. 13 shows the response of homozygous mutant mice, heterozygous mutant mice, and wild-type mice to a glucose challenge (GTT) after eight weeks on a high-fat diet.

After exposure to a high fat diet, homozygous mutants (−/−) gain less body weight than wild-type (+/+) and heterozygous mutant mice (−/+), as shown in FIG. 12. This difference in weight gain was present despite the fact that homozygous mutant mice consumed the same amount of food compared to wild-type and heterozygous mutant mice. When the GTT was repeated after high-fat diet challenge, it was again found that homozygous mutant mice had decreased fasting glucose levels and improved glucose tolerance when compared to wild-type and heterozygous control mice. As shown in FIG. 13, significant differences in glucose levels were seen between homozygous mutant mice (−/−) and wild-type control mice (+/+) at all time points ($p \leq 0.04$). Significant differences were also seen between homozygous mutant (−/−) and heterozygous mutant (−/+) mice at t=0 and t=30 minutes ($p \leq 0.02$).

A role for the glucagon receptor in diabetes and glucose tolerance is also supported by the data presented in the previous examples illustrating the effects of disruptions in glucagon receptors on pancreatic islet cells, body and organ weight, serum glucose levels, and body fat percentage.

As is apparent to one of skill in the art, various modifications of the above embodiments can be made without departing from the spirit and scope of this invention.

These modifications and variations are within the scope of this invention.

We claim:

1. A transgenic mouse whose genome comprises a homozygous disruption in the endogenous glucagon receptor gene, wherein the transgenic mouse exhibits, relative to a wild-type mouse, a pancreatic abnormality or a metabolic abnormality wherein the metabolic abnormality is selected from the group consisting of decreased fasting blood glucose level, increased glucose tolerance, decreased fasting insulin level, increased glucagon level, decreased body weight, decreased body fat percentage, decreased organ weight, decreased body size and dwarfism.

2. The transgenic mouse of claim 1, wherein the increased glucose tolerance is characterized by a decreased blood glucose level following glucose administration.

3. The transgenic mouse of claim 1, wherein the pancreatic abnormality is selected from the group consisting of pancreatic hyperplasia, pancreatic hypertrophy, increased cytoplasmic vacuolization of pancreatic cells, and increased cytoplasmic granularity of pancreatic cells.

4. The transgenic mouse of claim 1, wherein the pancreatic abnormality comprises a pancreatic adenoma.

5. The transgenic mouse of claim 1, wherein the pancreatic abnormality comprises an increase in number and size of pancreatic alpha cells.

6. The transgenic mouse of claim 1, wherein the pancreatic abnormality comprises a decrease in number of pancreatic beta cells.

7. A cell obtained from the transgenic mouse of claim 1.

* * * * *

SEQUENCE LISTING

<160> NUMBER OF SEQ ID NOS: 6

<210> SEQ ID NO 1
<211> LENGTH: 1944
<212> TYPE: DNA
<213> ORGANISM: Mus musculus

<400> SEQUENCE: 1

```
cagggtctcc cttgcaacct gaggagaggt gcacacactc tgaggaccta ggtgtgcaac      60
ctctgccaga tgtggggcgt ggctacccag aggcatgccc ctcacccagc tccactgtcc     120
ccacctgctg ctgctgctgt tggtgctgtc atgtctgcca gaggcacccc tgcccaggt     180
aatggacttt ttgtttgaga gtggaagct ctatagtgac caatgtcacc acaacctaag    240
cctgctgccc ccacctactg agctggtctg taacagaacc ttcgacaact actcctgctg    300
gcctgacacc cctcccaaca ccactgccaa catttcctgc cctggtacc taccttggtg     360
ccacaaagtg cagcaccgcc tagtgttcaa gaggtgtggg cccgatgggc agtgggttcg    420
agggccacgg gggcagccgt ggcgcaacgc ctcccaatgt cagttggatg atgaagagat    480
cgaggtccag aagggggtgg ccaagatgta tagcagccag caggtgatgt acaccgtggg    540
ctacagtctg tccctggggg ccttgctcct tgcgctggtc atcctgctgg gcctcaggaa    600
gctgcactgc acccgaaact acatccatgg gaacctgttt gcgtcctttg tgctcaaggc    660
tggctctgtg ttggtcatcg attggctgct gaagacacgg tacagccaga agattggcga    720
tgacctcagt gtgagcgtct ggctcagtga cggggcgatg gccggctgca gagtggccac    780
agtgatcatg cagtacggca tcatacccaa ctattgctgg ttgctggtag agggcgtgta    840
cctgtacagc ctgctgagcc ttgccacctt ctctgagagg agcttctttt ccctctacct    900
gggcattggc tggggtgcgc ccctgctgtt tgtcatcccc tgggtggtgg tcaagtgtct    960
gtttgagaat gttcagtgct ggaccagcaa tgacaacatg ggattctggt ggatcctgcg   1020
tattcctgtc ttcctggcct tactgatcaa ttttttcatc tttgtccaca tcattcaact   1080
tcttgtggcc aagctgcgtg cccatcagat gcactatgct gattacaagt tccggctggc   1140
caggtccacg ctgaccctca tccctctgct gggggtccac gaggtggtct ttgcctttgt   1200
gactgacgag catgcccaag gcaccctgcg ctccaccaag ctctttttg acctgttcct   1260
cagctccttc cagggtctgc tggtggctgt tctctactgt ttcctcaaca aggaggtgca   1320
ggcagagctg atgcggcgtt ggaggcaatg gcaagaaggc aaagctcttc aggaggaaag   1380
gttggccagc agccatggca gccacatggc cccagcaggg ccttgtcatg gtgatccctg   1440
tgagaaactt cagcttatga gtgcaggcag cagcagtggg actggctgtg tgccctctat   1500
ggagacctcg ctggccagta gtctcccaag gttggctgac agccccacct gaatctccac   1560
ttggagccta ggcaggttgt gttcaagaaa gggcctcaga ggacaaccca gagccagatg   1620
cccggccaag gttgaagagc caaagcagca agacagcagc ttgtactgtg cacactcccc   1680
taacctgtcc tagcctggca caggccacag tgacagagta ggggttggat atgatggaga   1740
agccatgtta tctatgaact ctgagtgttc ccatgtgtgt tgacatggtc cctgtaccca   1800
gatatgtcct tcagtaaaaa gctcgagtgg agctgctgca cagctcgtgg acagcaggct   1860
tgaagccccc agggacgggg tttgggaggc cggggatgag cagcacactc agcaggtgga   1920
gcgctagtgc aacccaggaa agaa                                           1944
```

```
<210> SEQ ID NO 2
<211> LENGTH: 485
<212> TYPE: PRT
<213> ORGANISM: Mus musculus

<400> SEQUENCE: 2
```

| | | | | | | | | | | | | | | | |
|---|---|---|---|---|---|---|---|---|---|---|---|---|---|---|---|
| Met | Pro | Leu | Thr | Gln | Leu | His | Cys | Pro | His | Leu | Leu | Leu | Leu | Leu | Leu |
| 1 | | | | 5 | | | | | 10 | | | | | 15 | |
| Val | Leu | Ser | Cys | Leu | Pro | Glu | Ala | Pro | Ser | Ala | Gln | Val | Met | Asp | Phe |
| | | | 20 | | | | | 25 | | | | | 30 | | |
| Leu | Phe | Glu | Lys | Trp | Lys | Leu | Tyr | Ser | Asp | Gln | Cys | His | His | Asn | Leu |
| | | 35 | | | | | 40 | | | | | 45 | | | |
| Ser | Leu | Leu | Pro | Pro | Thr | Glu | Leu | Val | Cys | Asn | Arg | Thr | Phe | Asp | |
| 50 | | | | | 55 | | | | 60 | | | | | | |
| Asn | Tyr | Ser | Cys | Trp | Pro | Asp | Thr | Pro | Asn | Thr | Thr | Ala | Asn | Ile | |
| 65 | | | | | 70 | | | | 75 | | | | | 80 | |
| Ser | Cys | Pro | Trp | Tyr | Leu | Pro | Trp | Cys | His | Lys | Val | Gln | His | Arg | Leu |
| | | | | 85 | | | | | 90 | | | | | 95 | |
| Val | Phe | Lys | Arg | Cys | Gly | Pro | Asp | Gly | Gln | Trp | Val | Arg | Gly | Pro | Arg |
| | | | 100 | | | | | 105 | | | | | 110 | | |
| Gly | Gln | Pro | Trp | Arg | Asn | Ala | Ser | Gln | Cys | Gln | Leu | Asp | Asp | Glu | Glu |
| | | | 115 | | | | | 120 | | | | | 125 | | |
| Ile | Glu | Val | Gln | Lys | Gly | Val | Ala | Lys | Met | Tyr | Ser | Ser | Gln | Gln | Val |
| | | 130 | | | | | 135 | | | | | 140 | | | |
| Met | Tyr | Thr | Val | Gly | Tyr | Ser | Leu | Ser | Leu | Gly | Ala | Leu | Leu | Leu | Ala |
| 145 | | | | | 150 | | | | 155 | | | | | 160 | |
| Leu | Val | Ile | Leu | Leu | Gly | Leu | Arg | Lys | Leu | His | Cys | Thr | Arg | Asn | Tyr |
| | | | | 165 | | | | | 170 | | | | | 175 | |
| Ile | His | Gly | Asn | Leu | Phe | Ala | Ser | Phe | Val | Leu | Lys | Ala | Gly | Ser | Val |
| | | | 180 | | | | | 185 | | | | | 190 | | |
| Leu | Val | Ile | Asp | Trp | Leu | Leu | Lys | Thr | Arg | Tyr | Ser | Gln | Lys | Ile | Gly |
| | | | 195 | | | | | 200 | | | | | 205 | | |
| Asp | Asp | Leu | Ser | Val | Ser | Val | Trp | Leu | Ser | Asp | Gly | Ala | Met | Ala | Gly |
| | | 210 | | | | | 215 | | | | | 220 | | | |
| Cys | Arg | Val | Ala | Thr | Val | Ile | Met | Gln | Tyr | Gly | Ile | Ile | Pro | Asn | Tyr |
| 225 | | | | | 230 | | | | 235 | | | | | 240 | |
| Cys | Trp | Leu | Leu | Val | Glu | Gly | Val | Tyr | Leu | Tyr | Ser | Leu | Leu | Ser | Leu |
| | | | | 245 | | | | | 250 | | | | | 255 | |
| Ala | Thr | Phe | Ser | Glu | Arg | Ser | Phe | Phe | Ser | Leu | Tyr | Leu | Gly | Ile | Gly |
| | | | 260 | | | | | 265 | | | | | 270 | | |
| Trp | Gly | Ala | Pro | Leu | Leu | Phe | Val | Ile | Pro | Trp | Val | Val | Lys | Cys | |
| | | 275 | | | | | 280 | | | | | 285 | | | |
| Leu | Phe | Glu | Asn | Val | Gln | Cys | Trp | Thr | Ser | Asn | Asp | Asn | Met | Gly | Phe |
| | | 290 | | | | | 295 | | | | | 300 | | | |
| Trp | Trp | Ile | Leu | Arg | Ile | Pro | Val | Phe | Leu | Ala | Leu | Leu | Ile | Asn | Phe |
| 305 | | | | | 310 | | | | 315 | | | | | 320 | |
| Phe | Ile | Phe | Val | His | Ile | Ile | Gln | Leu | Leu | Val | Ala | Lys | Leu | Arg | Ala |
| | | | | 325 | | | | | 330 | | | | | 335 | |
| His | Gln | Met | His | Tyr | Ala | Asp | Tyr | Lys | Phe | Arg | Leu | Ala | Arg | Ser | Thr |
| | | | 340 | | | | | 345 | | | | | 350 | | |
| Leu | Thr | Leu | Ile | Pro | Leu | Leu | Gly | Val | His | Glu | Val | Val | Phe | Ala | Phe |
| | | | 355 | | | | | 360 | | | | | 365 | | |
| Val | Thr | Asp | Glu | His | Ala | Gln | Gly | Thr | Leu | Arg | Ser | Thr | Lys | Leu | Phe |
| | | 370 | | | | | 375 | | | | | 380 | | | |

```
Phe Asp Leu Phe Leu Ser Ser Phe Gln Gly Leu Leu Val Ala Val Leu
385                 390                 395                 400

Tyr Cys Phe Leu Asn Lys Glu Val Gln Ala Glu Leu Met Arg Arg Trp
                405                 410                 415

Arg Gln Trp Gln Glu Gly Lys Ala Leu Gln Glu Arg Leu Ala Ser
            420                 425                 430

Ser His Gly Ser His Met Ala Pro Ala Gly Pro Cys His Gly Asp Pro
            435                 440                 445

Cys Glu Lys Leu Gln Leu Met Ser Ala Gly Ser Ser Gly Thr Gly
    450                 455                 460

Cys Val Pro Ser Met Glu Thr Ser Leu Ala Ser Ser Leu Pro Arg Leu
465                 470                 475                 480

Ala Asp Ser Pro Thr
                485

<210> SEQ ID NO 3
<211> LENGTH: 200
<212> TYPE: DNA
<213> ORGANISM: Artificial Sequence
<220> FEATURE:
<223> OTHER INFORMATION: Targeting Vector

<400> SEQUENCE: 3
gcagccgtgg cgcaacgcct cccaatgtca gttggatgat gaagagatcg aggtccaggt      60
cagctctgga gggtatgggg tggtgtcaca gcggggctgt gtggggccag gggatacggc     120
actgcccagc cccactcggc ctctggtttg cagaaggggg tggccaagat gtatagcagc     180
cagcaggtga cgtacaccgt                                                 200

<210> SEQ ID NO 4
<211> LENGTH: 200
<212> TYPE: DNA
<213> ORGANISM: Artificial Sequence
<220> FEATURE:
<223> OTHER INFORMATION: Targeting Vector

<400> SEQUENCE: 4
gaggtggtct ttgcctttgt gactgacgag catgcccaag gcaccctgcg ctccaccaag      60
ctcttttttg acctgttcct cagctccttc caggtgagtc tccatcatac cccacccctg     120
ggacccagag tgctgtcctt gaccactctc tttctccagg gtctgctggt ggctgttctc     180 tactgttttcc tcaacaagga                                                200

<210> SEQ ID NO 5
<211> LENGTH: 2034
<212> TYPE: DNA
<213> ORGANISM: Homo sapiens

<400> SEQUENCE: 5
ggatctggca gcgccgcgaa gacgagcggt caccggcgcc cgacccgagc gcgcccagag      60
gacggcgggg agccaagccg accccgagc agcgccgcgc gggccctgag gctcaaaggg     120
gcagcttcag gggaggacac cccactggcc aggacgcccc aggctctgct gctctgccac     180
tcagctgccc tcggaggagc gtacacacac accaggactg cattgcccca gtgtgcagcc     240
cctgccagat gtgggaggca gctagctgcc cagaggcatg ccccctgcc agccacagcg     300 accccctgctg ctgttgctgc tgctgctggc ctgccagcca caggtcccct ccgctcaggt     360
gatggacttc ctgtttgaga gtggaagct ctacggtgac cagtgtcacc acaacctgag     420
```

-continued

```
cctgctgccc cctcccacgg agctggtgtg caacagaacc ttcgacaagt attcctgctg       480
gccggacacc cccgccaata ccacggccaa catctcctgc ccctggtacc tgccttggca       540
ccacaaagtg caacaccgct tcgtgttcaa gagatgcggg cccgacggtc agtgggtgcg       600
tggaccccgg gggcagcctt ggcgtgatgc ctcccagtgc cagatggatg gcgaggagat       660
tgaggtccag aaggaggtgg ccaagatgta cagcagcttc caggtgatgt acacagtggg       720
ctacagcctg tccctggggg ccctgctcct cgccttggcc atcctggggg gcctcagcaa       780
gctgcactgc acccgcaatg ccatccacgc gaatctgttt gcgtccttcg tgctgaaagc       840
cagctccgtg ctggtcattg atgggctgct caggacccgc tacagccaga aaattggcga       900
cgacctcagt gtcagcacct ggctcagtga tggagcggtg ctggctgcc gtgtggccgc       960 ggtgttcatg caatatggca tcgtggccaa ctactgctgg ctgctggtgg agggcctgta      1020
cctgcacaac ctgctgggcc tggccaccct ccccgagagg agcttcttca gcctctacct      1080
gggcatcggc tgggggtgccc ccatgctgtt cgtcgtcccc tgggcagtgg tcaagtgtct      1140
gttcgagaac gtccagtgct ggaccagcaa tgacaacatg ggcttctggt ggatcctgcg      1200
gttccccgtc ttcctggcca tcctgatcaa cttcttcatc ttcgtccgca tcgttcagct      1260
gctcgtggcc aagctgcggg cacggcagat gcaccacaca gactacaagt ccggctggc      1320 caagtccacg ctgacccctca tccctctgct gggcgtccac gaagtggtct ttgccttcgt      1380
gacggacgag cacgcccagg gcaccctgcg ctccgccaag ctcttcttcg acctcttcct      1440
cagctccttc cagggcctgc tggtggctgt cctctactgc ttcctcaaca aggaggtgca      1500
gtcggagctg cggcggcgtt ggcaccgctg gcgcctgggc aaagtgctat gggaggagcg      1560
gaacaccagc aaccagggg cctcatcttc gcccggccac ggccctccca gcaaggagct      1620
gcagtttggg agggtggtg gcagccagga ttcatctgcg gagaccccct ggctggtgg      1680 cctccctaga ttggctgaga gccccttctg aaccctgctg ggaccccagc tagggctgga      1740
ctctggcacc cagaggcgtc gctggacaac ccagaactgg acgcccagct gaggctgggg      1800 gcggggagc caacagcagc cccaccttac ccccaccccc cagtgtggct gtctgcgaga      1860
ttgggcctcc tctccctgca cctgccttgt ccctggtgca gaggtgagca gaggagtcca      1920
gggcgggagt gggggctgtg ccgtgaactg cgtgccagtg tccccacgta tgtcggcacg      1980
tcccatgtgc atggaaatgt cctccaacaa taaagagctc aagtggtcac cgtg           2034
```

<210> SEQ ID NO 6
<211> LENGTH: 477
<212> TYPE: PRT
<213> ORGANISM: Homo sapiens

<400> SEQUENCE: 6

```
Met Pro Pro Cys Gln Pro Gln Arg Pro Leu Leu Leu Leu Leu Leu
  1               5                  10                  15

Leu Ala Cys Gln Pro Gln Val Pro Ser Ala Gln Val Met Asp Phe Leu
                 20                  25                  30

Phe Glu Lys Trp Lys Leu Tyr Gly Asp Gln Cys His His Asn Leu Ser
             35                  40                  45

Leu Leu Pro Pro Pro Thr Glu Leu Val Cys Asn Arg Thr Phe Asp Lys
         50                  55                  60

Tyr Ser Cys Trp Pro Asp Thr Pro Ala Asn Thr Thr Ala Asn Ile Ser
 65                  70                  75                  80

Cys Pro Trp Tyr Leu Pro Trp His His Lys Val Gln His Arg Phe Val
                 85                  90                  95
```

```
Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Ile
        115                 120                 125

Glu Val Gln Lys Glu Val Ala Lys Met Tyr Ser Ser Phe Gln Val Met
    130                 135                 140

Tyr Thr Val Gly Tyr Ser Leu Ser Leu Gly Ala Leu Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Thr Trp Leu Ser Asp Gly Ala Val Ala Gly Cys
    210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Val Val Pro Trp Ala Val Val Lys Cys Leu
        275                 280                 285

Phe Glu Asn Val Gln Cys Trp Thr Ser Asn Asp Asn Met Gly Phe Trp
    290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
            340                 345                 350

Thr Leu Ile Pro Leu Leu Gly Val His Glu Val Val Phe Ala Phe Val
        355                 360                 365

Thr Asp Glu His Ala Gln Gly Thr Leu Arg Ser Ala Lys Leu Phe Phe
    370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
                405                 410                 415

Arg Trp Arg Leu Gly Lys Val Leu Trp Glu Glu Arg Asn Thr Ser Asn
            420                 425                 430

His Arg Ala Ser Ser Ser Pro Gly His Gly Pro Pro Ser Lys Glu Leu
        435                 440                 445

Gln Phe Gly Arg Gly Gly Ser Gln Asp Ser Ser Ala Glu Thr Pro
    450                 455                 460

Leu Ala Gly Gly Leu Pro Arg Leu Ala Glu Ser Pro Phe
465                 470                 475
```